(12) United States Patent
Bingel et al.

(10) Patent No.: US 6,900,343 B1
(45) Date of Patent: May 31, 2005

(54) METHOD FOR THE PURIFICATION OF METALLOCENES

(75) Inventors: Carsten Bingel, Kriftel (DE); Patrik Müller, Kaiserslautern (DE); Hans-Herbert Brintzinger, Tägerwilen (CH); Hans-Robert-Hellmuth Damrau, Constance (DE)

(73) Assignee: Basell Polyolefine GmbH, Wesseling (DE)

( * ) Notice: Subject to any disclaimer, the term of this patent is extended or adjusted under 35 U.S.C. 154(b) by 0 days.

(21) Appl. No.: 09/856,695

(22) PCT Filed: Nov. 18, 1999

(86) PCT No.: PCT/EP99/08849

§ 371 (c)(1),
(2), (4) Date: May 24, 2001

(87) PCT Pub. No.: WO00/31089

PCT Pub. Date: Jun. 2, 2000

(30) Foreign Application Priority Data

Nov. 25, 1998 (DE) .......................................... 198 54 350
Jan. 11, 1999 (DE) .......................................... 199 00 585

(51) Int. Cl.$^7$ ............................. C07F 17/00; C07F 7/00; B01J 31/00
(52) U.S. Cl. ............................. 556/11; 556/12; 556/43; 556/53; 526/127; 526/160; 526/943; 502/103; 502/117; 502/120
(58) Field of Search ............................. 556/11, 12, 43, 556/53; 502/103, 117, 120; 526/127, 160, 943

(56) References Cited

U.S. PATENT DOCUMENTS

| | | | |
|---|---|---|---|
| 4,752,597 A | 6/1988 | Turner | 502/104 |
| 5,103,030 A | 4/1992 | Rohrmann et al. | 556/12 |
| 5,145,819 A | 9/1992 | Winter et al. | 502/117 |
| 5,304,614 A | 4/1994 | Winter et al. | 526/127 |
| 5,455,366 A | 10/1995 | Rohrmann et al. | 556/8 |
| 5,543,535 A | 8/1996 | Lisowsky | 556/11 |
| 5,556,997 A | 9/1996 | Strickler et al. | 556/11 |
| 5,770,752 A | 6/1998 | Kaufmann et al. | 556/11 |
| 5,770,753 A | 6/1998 | Kuber et al. | 556/11 |
| 6,291,596 B1 * | 9/2001 | Sasanuma et al. | 525/338 |
| 6,620,953 B1 | 9/2003 | Bingel et al. | 556/11 |

FOREIGN PATENT DOCUMENTS

| | | |
|---|---|---|
| DE | 195 47247 | 6/1997 |
| DE | 195 47248 | 6/1997 |
| EP | 287 666 | 10/1988 |
| EP | 320 762 | 6/1989 |
| EP | 416 815 | 3/1991 |
| EP | 485 823 | 5/1992 |
| EP | 537 686 | 4/1993 |
| EP | 549 900 | 7/1993 |
| EP | 576 970 | 1/1994 |
| EP | 669 340 | 8/1995 |
| WO | 87/03887 | 7/1997 |
| WO | 98/49331 | 9/1998 |

OTHER PUBLICATIONS

Repo et al., Journal of Organometallic Chemistry, vol. 541, pp. 363–366 (1997).*
Angew.Chem.1995,107,1255–1283,Brintzinger et al.
J.Org.Chem.,232(1982)233–247,Wild et al.Synthesis and Molecular Structures of Chiral . . . .
U.S. Appl. No. 09/701,658.

* cited by examiner

Primary Examiner—Porfirio Nazario-Gonzalez
(74) Attorney, Agent, or Firm—Keil & Weinkauf

(57) ABSTRACT

A process for purifying metallocenes in which a sparingly soluble metallocene halide is converted into a readily soluble and readily crystallizable metallocene by replacement of at least one halide ligand by an alternative negatively charged ligand and the metallocene obtained in this way is subsequently purified by crystallization.

14 Claims, No Drawings

METHOD FOR THE PURIFICATION OF METALLOCENES

The present invention relates to a process for purifying metallocenes, in which a sparingly soluble metallocene halide is converted into a readily soluble and readily crystallizable metallocene by replacement of at least one halide ligand by an alternative negatively charged ligand and the metallocene obtained in this way is subsequently purified by crystallization.

Metallocenes can, if appropriate in combination with one or more cocatalysts, be used as catalyst components for the polymerization and copolymerization of olefins. In particular, halogen-containing metallocenes are used as catalyst precursors which can be converted into a polymerization-active cationic metallocene complex by means of, for example, an aluminoxane (EP-A-129368).

The preparation of metallocenes is known per se (U.S. Pat. No. 4,752,597; U.S. Pat. No. 5,017,714; EP-A-320762; EP-A-416815; EP-A-537686; EP-A-669340; H. H. Brintzinger et al.; Angew. Chem., 107 (1995), 1255; H. H. Brintzinger et al., J. Organomet. Chem. 232 (1982), 233). For example, cyclopentadienyl-metal compounds can be reacted with halides of transition metals such as titanium, zirconium and hafnium. The metallocene dihalides formed, generally the metallocene dichlorides, are, in the case of the industrially interesting racemic ansa-bisindenyl-metallocenes which are required for the preparation of isotactic polypropylene (EP 0485823, EP 0549900, EP 0576970, WO 98/40331), generally sparingly soluble compounds. The crude products formed in the syntheses comprise not only the desired metallocenes but also considerable amounts of inorganic by-products (e.g. salts), organometallic by-products (e.g. isomers) and organic by-products (e.g. unreacted substituted cyclopentadienyl ligands). When metallocenes are used as catalyst components, both in homogeneous and in heterogeneous catalyst systems, the by-products adversely affect the catalyst activity in olefin polymerization.

For purifying the crude products comprising desired racemic ansa-bisindenyl-metallocene, methods by means of which inorganic, organometallic and organic by-products can be separated from the desired metallocene are known. In U.S. Pat. No. 5,455,366 and EP 576970, the racemic metallocenes are freed of lithium chloride, the meso isomer and organic impurities by extraction with methylene chloride and subsequent crystallization. In DE 19547247 and DE 19547248, the crude products from the metallocene synthesis are freed of the undesirable by-products by treatment with polar and/or protic solvents. In U.S. Pat. No. 5,556,997, a metallocene contaminated with tetrahydrofuran-containing by-products is purified further by treatment with tetrahydrofuran.

Although the major part of the by-products can be separated from the desired racemic metallocene using the known methods, the catalysts prepared using the metallocenes which have been purified in this way, in particular supported catalysts, frequently display unsatisfactory activity, or the proportion of undesirable low molecular weight polyolefins, known as extractables, is too high. If metallocenes purified by a further recrystallization are used as catalyst components, the abovementioned disadvantages in the polymerization can be avoided. However, large amounts of solvent are required because of the sparing solubility of the industrially relevant ansa-bisindenyl-metallocene dichlorides. Simple recrystallization of the metallocene dichlorides is thus an uneconomical process step.

It is an object of the present invention to find an economical purification process by means of which metallocenes of the required quality can be obtained.

We have found that this object is achieved by a simple process in which the sparingly soluble, insufficiently pure metallocene dihalides are converted into more soluble and readily crystallizable metallocenes by replacement of at least one halide ligand and the new metallocenes prepared in this way are obtained in purified form by removing insoluble constituents by crystallization.

The present invention accordingly provides a process for purifying compounds of the formula (Ia)

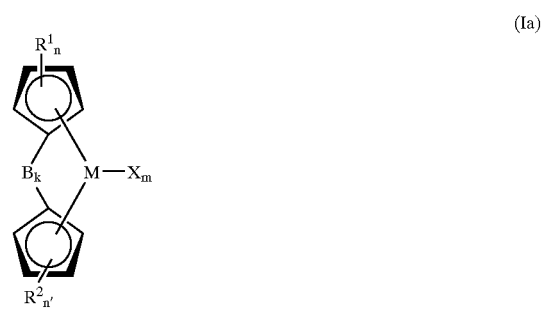

(Ia)

where
M is a metal of transition group III, IV, V or VI of the Periodic Table of the Elements, in particular Ti, Zr or Hf, particularly preferably zirconium,
$R^1$ are identical or different and are each a radical $Si(R^{12})_3$, where $R^{12}$ are identical or different and are each a hydrogen atom or a $C_1$–$C_{40}$ group, preferably $C_1$–$C_{20}$-alkyl, $C_1$–$C_{10}$-fluoroalkyl, $C_1$–$C_{10}$-alkoxy, $C_6$–$C_{20}$-aryl, $C_6$–$C_{10}$-fluoroaryl, $C_6$–$C_{10}$-aryloxy, $C_2$–$C_{10}$-alkenyl, $C_7$–$C_{40}$-arylalkyl, $C_7$–$C_{40}$-alkylaryl or $C_8$–$C_{40}$-arylalkenyl,
or $R^1$ is a $C_1$–$C_{30}$ group, preferably $C_1$–$C_{25}$-alkyl such as methyl, ethyl, tert-butyl, cyclohexyl or octyl, $C_2$–$C_{25}$-alkenyl, $C_3$–$C_{15}$-alkylalkenyl, $C_6$–$C_{24}$-aryl, $C_5$–$C_{24}$-heteroaryl, $C_7$–$C_{30}$-arylalkyl, $C_7$–$C_{30}$-alkylaryl, fluorinated $C_1$–$C_{25}$-alkyl, fluorinated $C_6$–$C_{24}$-aryl, fluorinated $C_7$–$C_{30}$-arylalkyl, fluorinated $C_7$–$C_{30}$-alkylaryl or $C_1$–$C_{12}$-alkoxy,
or two or more radicals $R^1$ may be joined to one another in such a way that the radicals $R^1$ and the atoms of the cyclopentadienyl ring which connect them form a $C_4$–$C_{24}$-ring system which may in turn be substituted,
$R^2$ are identical or different and are each a radical $Si(R^{12})_3$, where $R^{12}$ are identical or different and are each a hydrogen atom or a $C_1$–$C_{40}$ group, preferably $C_1$–$C_{20}$-alkyl, $C_1$–$C_{10}$-fluoroalkyl, $C_1$–$C_{10}$-alkoxy, $C_6$–$C_{14}$-aryl, $C_6$–$C_{10}$-fluoroaryl, $C_6$–$C_{10}$-aryloxy, $C_2$–$C_{10}$-alkenyl, $C_7$–$C_{40}$-arylalkyl, $C_7$–$C_{40}$-alkylaryl or $C_8$–$C_{40}$-arylalkenyl,
or $R^2$ is a $C_1$–$C_{30}$ group, preferably $C_1$–$C_{25}$-alkyl such as methyl, ethyl, tert-butyl, cyclohexyl or octyl, $C_2$–$C_{25}$-alkenyl, $C_3$–$C_{15}$-alkylalkenyl, $C_6$–$C_{24}$-aryl, $C_5$–$C_{24}$-heteroaryl, $C_7$–$C_{30}$-arylalkyl, $C_7$–$C_{30}$-alkylaryl, fluorinated $C_1$–$C_{25}$-alkyl, fluorinated $C_6$–$C_{24}$-aryl, fluorinated $C_7$–$C_{30}$-arylalkyl, fluorinated $C_7$–$C_{30}$-alkylaryl or $C_1$–$C_{12}$-alkoxy,
or two or more radicals $R^2$ may be joined to one another in such a way that the radicals $R^2$ and the atoms of the cyclopentadienyl ring which connect them form a $C_4$–$C_{24}$ ring system which may in turn be substituted,
X is a halogen atom, in particular chlorine,
n is from 1 to 5 when k=0, and n is from 0 to 4 when k=1,
n' is from 1 to 5 when k=0, and n' is from 0 to 4 when k=1,
m is from 1 to 4, preferably 2,
k is zero or 1, where the metallocene is unbridged when k=0 and is bridged when k=1, with preference being given to k=1, and B is a bridging structural element between the two cyclopentadienyl rings, comprising the steps:

a) reacting the compound of the formula (Ia) with a ligand exchange component $$M^1YR^3$$

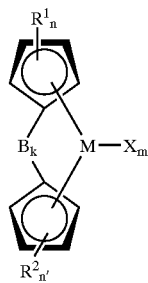
(Ia)

where

M$^1$ is a cation or a cationic fragment, in particular Li, Na, K, MgCl, MgBr, MgI, or is an ammonium cation corresponding to an amine, R$^3$ is hydrogen or a C$_1$–C$_{40}$ group, preferably C$_1$–C$_{25}$-alkyl such as methyl, ethyl, n-propyl, isopropyl tert-butyl, cyclohexyl or octyl, C$_2$–C$_{25}$-alkenyl, C$_3$–C$_{15}$-alkylalkenyl, C$_6$–C$_{24}$-aryl, C$_5$–C$_{24}$-heteroaryl such as pyridyl, furyl or quinolyl, C$_7$–C$_{30}$-arylalkyl, C$_7$–C$_{30}$-alkylaryl, fluorinated C$_1$–C$_{25}$-alkyl, fluorinated C$_6$–C$_{24}$-aryl, fluorinated C$_7$–C$_{30}$-arylalkyl or fluorinated C$_7$–C$_{30}$-alkylaryl, Y is an element of main group 6 of the Periodic Table of the Elements, in particular oxygen or sulfur, or a fragment CR$^3_2$, NR$^3$, NR$^3$(CO)—, NR$^3$(SO$_2$)—, PR$^3$, (=O)R$^3$, O(CO)— or O(SO$_2$)—, to form the compound of the formula (I)

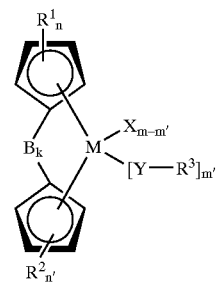
(I)

where

M, R$^1$, R$^2$, R$^3$, X, Y, n, n', m, k, B and R$^{12}$ are as defined above and m' is from 1 to 4, preferably 1 or 2, with the compound of the formula M$^1$X, where M$^1$ and X are as defined above, being eliminated, in an inert solvent or solvent mixture, b) if desired, separating off solid residues of the formula M$^1$X c) if desired, separating off the inert solvent or solvent mixture, d) recrystallizing the compound of the formula (I) from an aprotic hydrocarbon, e) separating the compound of the formula (I) from the mother liquor.

In the purification process of the present invention, a metallocene of the formula (Ia) is converted into a metallocene of the formula (I) and subsequently recrystallized.

In the process of the present invention, the compounds of the formulae (Ia) and (I) are

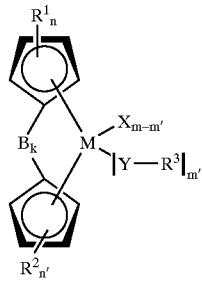
(I)

where

M is a metal of transition group III, IV, V or VI of the Periodic Table of the Elements, in particular Ti, Zr or Hf, particularly preferably zirconium, R$^1$ are identical or different and are each a radical Si(R$^{12}$)$_3$, where R$^{12}$ are identical or different and are each a hydrogen atom or a C$_1$–C$_{40}$ group, preferably C$_1$–C$_{20}$-alkyl, C$_1$–C$_{10}$-fluoroalkyl, C$_1$–C$_{10}$-alkoxy, C$_6$–C$_{20}$-aryl, C$_6$–C$_{10}$-fluoroaryl, C$_6$–C$_{10}$-aryloxy, C$_2$–C$_{10}$-alkenyl, C$_7$–C$_{40}$-arylalkyl, C$_7$–C$_{40}$-alkylaryl or C$_8$–C$_{40}$-arylalkenyl, or R$^1$ is a C$_1$–C$_{30}$ group, preferably C$_1$–C$_{25}$-alkyl such as methyl, ethyl, tert-butyl, cyclohexyl or octyl, C$_2$–C$_{25}$-alkenyl, C$_3$–C$_{15}$-alkylalkenyl, C$_6$–C$_{24}$-aryl, C$_5$–C$_{24}$-heteroaryl, C$_7$–C$_{30}$-arylalkyl, C$_7$–C$_{30}$-alkylaryl, fluorinated C$_1$–C$_{25}$-alkyl, fluorinated C$_6$–C$_{24}$-aryl, fluorinated C$_7$–C$_{30}$-arylalkyl, fluorinated C$_7$–C$_{30}$-alkylaryl or C$_1$–C$_{12}$-alkoxy, or two or more radicals R$^1$ may be joined to one another in such a way that the radicals R$^1$ and the atoms of the cyclopentadienyl ring which connect them form a C$_4$–C$_{24}$-ring system which may in turn be substituted, R$^2$ are identical or different and are each a radical Si(R$^{12}$)$_3$, where R$^{12}$ are identical or different and are each a hydrogen atom or a C$_1$–C$_{40}$ group, preferably C$_1$–C$_{20}$-alkyl, C$_1$–C$_{10}$-fluoroalkyl, C$_1$–C$_{10}$-alkoxy, C$_6$–C$_{14}$-aryl, C$_6$–C$_{10}$-fluoroaryl, C$_6$–C$_{10}$-aryloxy, C$_2$–C$_{10}$-alkenyl, C$_7$–C$_{40}$-arylalkyl, C$_7$–C$_{40}$-alkylaryl or C$_8$–C$_{40}$-arylalkenyl, or R$^2$ is a C$_1$–C$_{30}$ group, preferably C$_1$–C$_{25}$-alkyl such as methyl, ethyl, tert-butyl, cyclohexyl or octyl, C$_2$–C$_{25}$-alkenyl, C$_3$–C$_{15}$-alkylalkenyl, C$_6$–C$_{24}$-aryl, C$_5$–C$_{24}$-heteroaryl, C$_7$–C$_{30}$-arylalkyl, C$_7$–C$_{30}$-alkylaryl, fluorinated C$_1$–C$_{25}$-alkyl, fluorinated C$_6$–C$_{24}$-aryl, fluorinated C$_7$–C$_{30}$-arylalkyl, fluorinated C$_7$–C$_{30}$-alkylaryl or C$_1$–C$_{12}$-alkoxy, or two or more radicals R$^2$ may be joined to one another in such a way that the radicals R$^2$ and the atoms of the cyclopentadienyl ring which connect them form a C$_4$–C$_{24}$ ring system which may in turn be substituted, R$^3$ are identical or different and are each hydrogen or a C$_1$–C$_{40}$ group, preferably C$_1$–C$_{25}$-alkyl such as methyl, ethyl, n-propyl, isopropyl, tert-butyl, cyclohexyl or octyl, C$_2$–C$_{25}$-alkenyl, C$_3$–C$_{15}$-alkylalkenyl, C$_6$–C$_{24}$-aryl, $C_5-C_{24}$-heteroaryl such as pyridyl, furyl or quinolyl, $C_7-C_{30}$-arylalkyl, $C_7-C_{30}$-alkylaryl, fluorinated $C_1-C_{25}$-alkyl, fluorinated $C_6-C_{24}$-aryl, fluorinated $C_7-C_{30}$-arylalkyl or fluorinated $C_7-C_{30}$-alkylaryl, X is a halogen atom, in particular chlorine, Y is an element of main group VI of the Periodic Table of the Elements, in particular oxygen or sulfur, or a fragment $CR^3{}_2$, $NR^3$, $NR^3(CO)$—, $NR^3(SO_2)$—, $PR^3$, $P(=O)R^3$, $O(CO)$— or $O(SO_2)$—, n is from 1 to 5 when k=0, and n is from 0 to 4 when k=1, n' is from 1 to 5 when k=0, and n' is from 0 to 4 when k=1, m is from 1 to 4, preferably 2, m' is from 1 to 4, preferably 1 or 2, k is zero or 1, where the metallocene is unbridged when k=0 and is bridged when k=1, with preference being given to k=1, and B is a bridging structural element between the two cyclopentadienyl rings.

Examples of B are $M^3R^{13}R^{14}$ groups, where $M^3$ is carbon, silicon, germanium or tin and $R^{13}$ and $R^{14}$ are identical or different and are each a $C_1-C_{20}$-hydrocarbon-containing group such as $C_1-C_{10}$-alkyl, $C_6-C_{14}$-aryl or trimethylsilyl. B is preferably $CH_2$, $CH_2CH_2$, $CH(CH_3)CH_2$, $CH(C_4H_9)C(CH_3)_2$, $C(CH_3)_2$, $(CH_3)_2Si$, $(CH_3)_2Ge$, $(CH_3)_2Sn$, $(C_6H_5)_2Si$, $(C_6H_5)(CH_3)Si$, $Si(CH_3)(SiR^{20}R^{21}R^{22})$, $(C_6H_5)_2Ge$, $(C_6H_5)_2Sn$, $(CH_2)_4Si$, $CH_2Si(CH_3)_2$, o-$C_6H_4$ or 2,2'-$(C_6H_4)_2$, where $R^{20}$, $R^{21}$, $R^{22}$ are identical or different and are each a $C_1-C_{20}$-hydrocarbon-containing group such as $C_1-C_{10}$-alkyl or $C_6-C_{14}$-aryl. It is also possible for B together with one or more radicals $R^1$ and/or $R^2$ to form a monocyclic or polycyclic ring system.

In the purification process of the present invention, metallocene halides of the formula (Ia) are reacted with a ligand exchange component to convert them directly in one reaction step into metallocenes of the formula (I) which, owing to their good solubility, are obtained in a high space-time yield and in the required purity by crystallization.

Preference is given to a purification process in which a bridged metallocene of the formula (I) is formed from a bridged metallocene of the formula (Ia), in particular a bridged metallocene in which k is 1 and one or both cyclopentadienyl rings are substituted in such a way that they form an indenyl ring. The indenyl ring is preferably substituted, in particular in the 2 position, 4 position, 2,4,5 positions, 2,4,6 positions, 2,4,7 positions or 2,4,5,6 positions, by $C_1-C_{20}$ groups such as $C_1-C_{18}$-alkyl or $C_6-C_{18}$-aryl, where two or more substituents of the indenyl ring may also together form a ring system.

Particular preference is given to a purification process in which a bridged metallocene of the formula (IIa) is converted into a bridged metallocene of the formula (II),

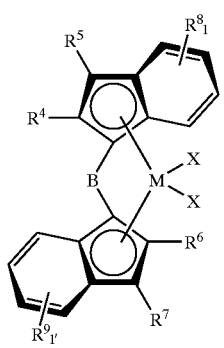

(IIa)

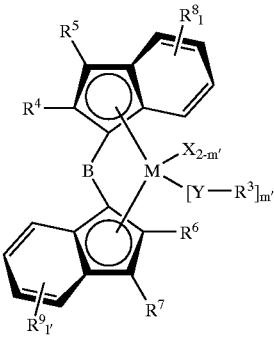

(II)

where

M is Ti, Zr or Hf, particularly preferably zirconium, $R^3$ are identical or different and are each a hydrogen or a $C_1-C_{30}$ group, preferably $C_1-C_{10}$-alkyl such as methyl, ethyl, n-propyl, isopropyl, tert-butyl, cyclohexyl or octyl, $C_2-C_{16}$-alkenyl, $C_6-C_{24}$-aryl, $C_5-C_{24}$-heteroaryl such as pyridyl, furyl or quinolyl, $C_7-C_{30}$-arylalkyl, $C_7-C_{30}$-alkylaryl, fluorinated $C_6-C_{24}$-aryl, fluorinated $C_7-C_{30}$-arylalkyl or fluorinated $C_7-C_{30}$-alkylaryl, $R^4$, $R^6$ are identical or different and are each a hydrogen atom or a $C_1-C_{20}$ group, preferably $C_1-C_{18}$-alkyl such as methyl, ethyl, n-butyl, cyclohexyl or octyl, $C_2-C_{10}$-alkenyl, $C_3-C_{15}$-alkylalkenyl, $C_6-C_{18}$-aryl, $C_5-C_{18}$-heteroaryl such as pyridyl, furyl or quinolyl, $C_7-C_{20}$-arylalkyl, $C_7-C_{20}$-alkylaryl, fluorinated $C_1-C_{12}$-alkyl, fluorinated $C_6-C_{18}$-aryl, fluorinated $C_7-C_{20}$-arylalkyl or fluorinated $C_7-C_{20}$-alkylaryl, $R^5$, $R^7$ are identical or different and are each a hydrogen atom or a $C_1-C_{20}$ group, preferably $C_1-C_{18}$-alkyl such as methyl, ethyl, n-butyl, cyclohexyl or octyl, $C_2-C_{10}$-alkenyl, $C_3-C_{15}$-alkylalkenyl, $C_6-C_{18}$-aryl, $C_5-C_{18}$-heteroaryl such as pyridyl, furyl or quinolyl, $C_7-C_{20}$-arylalkyl, $C_7-C_{20}$-alkylaryl, fluorinated $C_1-C_{12}$-alkyl, fluorinated $C_6-C_{18}$-aryl, fluorinated $C_7-C_{20}$-arylalkyl or fluorinated $C_7-C_{20}$-alkylaryl, $R^8$ and $R^9$ are identical or different and are each a hydrogen atom, a halogen atom or a $C_1-C_{20}$ group, preferably a linear or branched $C_1-C_{18}$-alkyl group such as methyl, ethyl, tert-butyl, cyclohexyl or octyl, $C_2-C_{10}$-alkenyl, $C_3-C_{15}$-alkylalkenyl, a $C_6-C_{18}$-aryl group which may be substituted, in particular phenyl, tolyl, xylyl, tert-butylphenyl, ethylphenyl, di-tert-butylphenyl, naphthyl, acenaphthyl, phenanthrenyl or anthracenyl, $C_5-C_{18}$-heteroaryl such as pyridyl, furyl or quinolyl, $C_7-C_{20}$-arylalkyl, $C_7-C_{20}$-alkylaryl, fluorinated $C_1-C_{12}$-alkyl, fluorinated $C_6-C_{18}$-aryl, fluorinated $C_7-C_{20}$-arylalkyl or fluorinated $C_7-C_{20}$-alkylaryl, and two radicals $R^8$ or $R^9$ may form a monocyclic or polycyclic ring system which may in turn be substituted, X is a halogen atom, in particular chlorine, Y is an element of main group VI of the Periodic Table of the Elements, in particular oxygen or sulfur, or a fragment $CR^3{}_2$, $NR^3$, $NR^3(CO)$—, $NR^3(SO_2)$—, $PR^3$, $P(=O)R^3$, $O(CO)$— or $O(SO_2)$—, l, l' are identical or different and are each an integer from zero to 4, preferably 1 or 2, particularly preferably 1, m' is 1 or 2, B is a bridging structural element between the two indenyl radicals.

Examples of B are $M^3R^{13}R^{14}$ groups, where $M^3$ is carbon, silicon, germanium or tin, preferably carbon or silicon, and $R^{13}$ and $R^{14}$ are identical or different and are each hydrogen or a $C_1$–$C_{20}$-hydrocarbon-containing group such as $C_1$–$C_{10}$-alkyl, $C_6$–$C_{14}$-aryl or trimethylsilyl. B is preferably $CH_2$, $CH_2CH_2$, $CH(CH_3)CH_2$, $CH(C_4H_9)C(CH_3)_2$, $C(CH_3)_2$, $(CH_3)_2Si$, $(CH_3)_2Ge$, $(CH_3)_2Sn$, $(C_6H_5)_2C$, $(C_6H_5)_2Si$, $(C_6H_5)(CH_3)Si$, $Si(CH_3)(SiR^{20}R^{21}R^{22})$, $(C_6H_5)_2Ge$, $(C_6H_5)_2Sn$, $(CH_2)_4Si$, $CH_2Si(CH_3)_2$, o-$C_6H_4$ or 2,2'-$(C_6H_4)_2$, where $R^{20}$, $R^{21}$, $R^{22}$ are identical or different and are each a $C_1$–$C_{20}$-hydrocarbon-containing group such as $C_1$–$C_{10}$-alkyl or $C_6$–$C_{14}$-aryl.

Very particular preference is given to a purification process in which a bridged metallocene of the formula (IIa) is converted into a bridged metallocene of the formula (II), where M is zirconium, $R^3$ are identical or different and are each hydrogen or a $C_1$–$C_{30}$ group, preferably $C_1$–$C_{10}$-alkyl such as methyl, ethyl, n-propyl, isopropyl, tert-butyl, cyclohexyl or octyl, $C_2$–$C_{12}$-alkenyl, $C_6$–$C_{24}$-aryl, $C_5$–$C_{24}$-heteroaryl such as pyridyl, furyl or quinolyl, $C_7$–$C_{30}$-arylalkyl, $C_7$–$C_{30}$-alkylaryl, fluorinated $C_6$–$C_{24}$-aryl, fluorinated $C_7$–$C_{30}$-arylalkyl or fluorinated $C_7$–$C_{30}$-alkylaryl, $R^4$, $R^6$ are identical or different and are each a hydrogen atom or a $C_1$–$C_{12}$-alkyl group, preferably an alkyl group such as methyl, ethyl, n-butyl or octyl, particularly preferably methyl or ethyl, $R^5$, $R^7$ are hydrogen atoms, $R^8$ and $R^9$ are identical or different and are each a hydrogen atom, a halogen atom or a $C_1$–$C_{20}$ group, preferably a linear or branched $C_1$–$C_8$-alkyl group such as methyl, ethyl, tert-butyl, cyclohexyl or octyl, $C_2$–$C_6$-alkenyl, $C_3$–$C_6$-alkylalkenyl, a $C_6$–$C_{18}$-aryl group which may be substituted, in particular phenyl, tolyl, xylyl, tert-butylphenyl, ethylphenyl, di-tert-butylphenyl, naphthyl, acenaphthyl, phenanthrenyl or anthracenyl, $C_5$–$C_{18}$-heteroaryl such as pyridyl, furyl or quinolyl, $C_7$–$C_{12}$-arylalkyl, $C_7$–$C_{12}$-alkylaryl, fluorinated $C_1$–$C_8$-alkyl, fluorinated $C_6$–$C_{18}$-aryl, fluorinated $C_7$–$C_{12}$-arylalkyl or fluorinated $C_7$–$C_{12}$-alkylaryl, X is chlorine, Y is an element of main group VI of the Periodic Table of the Elements, in particular oxygen or sulfur, or a fragment $CR^3_2$, $NR^3$, $NR^3(CO)$—, $NR^3(SO_2)$—, $PR^3$, $P(=O)R^3$, $O(CO)$— or $O(SO_2)$—, l, l' are identical or different and are each an integer from zero to 4, preferably 1 or 2, particularly preferably 1, m' is 1 or 2, preferably 1, and B is a bridging structural element between the two indenyl radicals and is preferably $(CH_3)_2Si$, $(CH_3)_2Ge$, $(C_6H_5)_2Si$, $(C_6H_5)(CH_3)Si$, $CH_2CH_2$, $CH(CH_3)CH_2$, $CH(C_4H_9)C(CH_3)_2$, $CH_2$, $C(CH_3)_2$, $(C_6H_5)_2C$, particularly preferably $(CH_3)_2Si$, $CH_2$ and $CH_2CH_2$.

When Y=oxygen and $R^3$ is alkenyl, individual $CH_2$ units in the alkenyl radical can be replaced by C=O, C(O)O or C(O)$NR^3$.

The metallocenes of the formulae I and II obtained in the purification process of the present invention display a significantly better solubility in inert organic solvents than do the corresponding metallocenes of the formulae (Ia) and (IIa). For the purposes of the present invention, a significantly better solubility means that the molar concentrations in organic solvents are at least doubled, preferably more than quadrupled and very particularly preferably increased by a factor of more than eight.

As inert organic solvents for metallocenes, use is made of the usual aliphatic or aromatic hydrocarbons and also halogen-containing, oxygen-containing or nitrogen-containing hydrocarbons. Nonlimiting examples of the individual classes of solvent are heptane, toluene, dichlorobenzene, methylene chloride, tetrahydrofuran or triethylamine.

The purification process of the present invention is preferably carried out using metallocenes of the formulae (Ia) and (IIa), i.e. racemic metallocene dichlorides as are mentioned in EP-A-0485823, EP-A-0549900, EP-A-0576970, WO 98/22486 and WO 98/40331. These are hereby incorporated by reference into the present description.

However, it is also possible to use any mixtures of the racemic metallocene dichloride of the formula (IIIa) with the corresponding meso-metallocene dichloride of the formula (IIIb), where the symbols and indices are defined as under formula (IIa), in the purification process of the present invention.

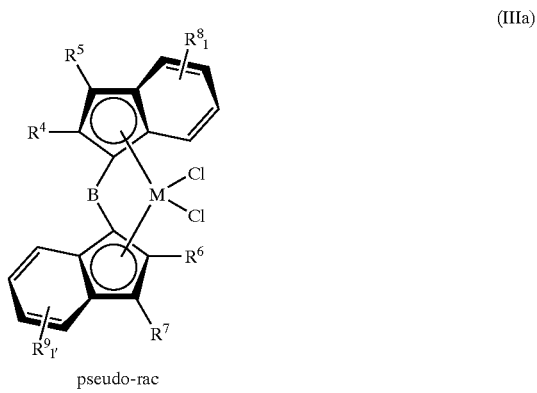

(IIIa)

pseudo-rac

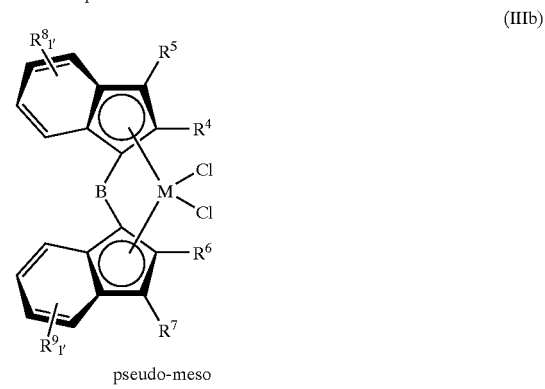

(IIIb)

pseudo-meso

The metallocenes of the formulae (Ia) and (IIa) used in the purification process of the present invention, preferably the metallocenes of the formula (IIa), can be used in the form in which they are obtained directly from the metallocene synthesis together with the inorganic, organometallic and organic by-products, or in the form in which they can be obtained after separating off a large part of the by-products by one of the abovementioned known purification methods.

Illustrative but nonlimiting examples of metallocenes of the formula (Ia) or (IIa) which can be used in the purification process of the present invention are:

dimethylsilanediylbis(indenyl)zirconium dichloride dimethylsilanediylbis(2-methylindenyl)zirconium dichloride methylidenebis(2-methylindenyl)zirconium dichloride isopropylidenebis(2-methylindenyl)zirconium dichloride dimethylsilanediylbis(2-methylbenzoindenyl)zirconium dichloride dimethylsilanediylbis(4-naphthylindenyl)zirconium dichloride dimethylsilanediylbis(2-methyl-4-(1-naphthyl)indenyl)zirconium dichloride methylidenebis(2-methyl-4-(1-naphthyl)indenyl)zirconium dichloride isopropylidenebis(2-methyl-4-(1-naphthyl)indenyl)zirconium dichloride dimethylsilanediylbis(2-methyl-4-(2-naphthyl)indenyl) zirconium dichloride
dimethylsilanediylbis(2-methyl-4-phenylindenyl)zirconium dichloride
methylidenebis(2-methyl-4-phenylindenyl)zirconium dichloride
isopropylidenebis(2-methyl-4-phenylindenyl)zirconium dichloride
dimethylsilanediylbis(2-methyl-4-t-butylindenyl)zirconium dichloride
dimethylsilanediylbis(2-methyl-4-isopropylindenyl) zirconium dichloride
dimethylsilanediylbis(2-methyl-4-ethylindenyl)zirconium dichloride
dimethylsilanediylbis(2,4-dimethylindenyl)zirconium dichloride
dimethylsilanediylbis(2-ethylindenyl)zirconium dichloride
dimethylsilanediylbis(2-ethyl-4-ethylindenyl)zirconium dichloride
dimethylsilanediylbis(2-ethyl-4-phenylindenyl)zirconium dichloride
dimethylsilanediylbis(2-methyl-4,5-benzoindenyl) zirconium dichloride
methylidenebis(2-methyl-4,5-benzoindenyl)zirconium dichloride
isopropylidenebis(2-methyl-4,5-benzoindenyl)zirconium dichloride
dimethylsilanediylbis(2-methyl-4,6-diisopropylindenyl) zirconium dichloride
dimethylsilanediylbis(2-methyl-4,5-diisopropylindenyl) zirconium dichloride
dimethylsilanediylbis(2,4,6-trimethylindenyl)zirconium dichloride
dimethylsilanediylbis(2,5,6-trimethylindenyl)zirconium dichloride
dimethylsilanediylbis(2,4,7-trimethylindenyl)zirconium dichloride
dimethylsilanediylbis(2-methyl-5-isobutylindenyl) zirconium dichloride
dimethylsilanediylbis(2-methyl-5-t-butylindenyl)zirconium dichloride
methyl(phenyl)silanediylbis(2-methyl-4-phenylindenyl) zirconium dichloride
methyl(phenyl)silanediylbis(2-methyl-4,6-diisopropylindenyl)-zirconium dichloride
methyl(phenyl)silanediylbis(2-methyl-4-isopropylindenyl) zirconium dichloride
methyl(phenyl)silanediylbis(2-methyl-4,5-benzoindenyl) zirconium dichloride
methyl(phenyl)silanediylbis(2-methylindenyl)zirconium dichloride
methyl(phenyl)silanediylbis(2-methyl-5-isobutylindenyl) zirconium dichloride
1,2-ethanediylbis(2-methyl-4-phenylindenyl)zirconium dichloride
1,4-butanediylbis(2-methyl-4-phenylindenyl)zirconium dichloride
1,2-ethanediylbis(2-methyl-4,6-diisopropylindenyl) zirconium dichloride
1,4-butanediylbis(2-methyl-4-isopropylindenyl)zirconium dichloride
1,4-butanediylbis(2-methyl-4,5-benzoindenyl)zirconium dichloride
1,2-ethanediylbis(2-methyl-4,5-benzoindenyl)zirconium dichloride
1,2-ethanediylbis(2,4,7-trimethylindenyl)zirconium dichloride
1,2-ethanediylbis(2-methylindenyl)zirconium dichloride
1,4-butanediylbis(2-methylindenyl)zirconium dichloride
[4-($\eta^5$-cyclopentadienyl)-4,6,6-trimethyl($\eta^5$-4,5-tetrahydropentalene)]zirconium dichloride
[4-($\eta^5$-3'-trimethylsilylcyclopentadienyl)-4,6,6-trimethyl ($\eta^5$-4,5-tetrahydropentalene)]zirconium dichloride
[4-($\eta^5$-3'-isopropylcyclopentadienyl)-4,6,6-trimethyl-($^5$-4,5-tetrahydropentalene)]zirconium dichloride
[4-($\eta^5$-cyclopentadienyl)-4,7,7-trimethyl-($\eta^5$-4,5,6,7-tetrahydroindenyl)]zirconium dichloride
[4-($\eta^5$-3'-tert-butylcyclopentadienyl)-4,7,7-trimethyl($\eta^5$-4,5,6,7-tetrahydroindenyl)]zirconium dichloride
4-($\eta^5$-3'-methylcyclopentadienyl)-4,7,7-trimethyl-($^5$-4,5,6,7-tetrahydroindenyl)]zirconium dichloride
4-($\eta^5$-3'-trimethylsilylcyclopentadienyl)-2-trimethylsilyl-4,7,7-trimethyl-($\eta^5$-4,5,6,7-tetrahydroindenyl))zirconium dichloride
dimethylsilanediylbis(tetrahydroindenyl)zirconium dichloride
isopropylidenebisindenylzirconium dichloride
isopropylidenecyclopentadienyl-9-fluorenylzirconium dichloride
isopropylidenecyclopentadienylindenylzirconium dichloride
diphenylmethylidene(cyclopentadienyl)-(9-fluorenyl) zirconium dichloride
diphenylmethylidene(3-methylcyclopentadienyl)-(9-fluorenyl)-zirconium dichloride
diphenylmethylidene(3-isopropylcyclopentadienyl)-(9-fluorenyl)-zirconium dichloride
diphenylmethylidene(3-tert-butylcyclopentadienyl)-(9-fluorenyl)-zirconium dichloride
dimethylsilanediylcyclopentadienyl-9-fluorenylzirconium dichloride
diphenylsilanediylcyclopentadienyl-9-fluorenylzirconium dichloride
dimethylsilanediylbis(2-methyl-4-(tert-butylphenylindenyl)-zirconium dichloride
dimethylsilanediylbis(2-methyl-4-(4-trifluoromethylphenyl-indenyl)zirconium dichloride
dimethylsilanediylbis(2-methyl-4-(4-methoxyphenylindenyl)-zirconium dichloride
dimethylsilanediylbis(2-ethyl-4-(4-methylphenylindenyl) zirconium dichloride
dimethylsilanediylbis(2-ethyl-4-(4-ethylphenylindenyl) zirconium dichloride
dimethylsilanediylbis(2-ethyl-4-(4-trifluormethylphenylindenyl)-zirconium dichloride
dimethylsilanediylbis(2-ethyl-4-(4-methoxyphenylindenyl) zirconium dichloride
dimethylsilanediylbis(2-methyl-4-(4-tert-butylphenyl indenyl)-zirconium dichloride
dimethylsilanediylbis(2-methyl-4-(3',5'-di-tert-butylphenyl)-indenyl)zirconium dichloride
methylidenebis(2-methyl-4-(4'-tert-butylphenyl)indenyl) zirconium dichloride
isopropylidenebis(2-methyl-4-(4'-tert-butylphenyl) indenyl)-zirconium dichloride
dimethylsilanediylbis(2-methyl-4-(4'-methylphenyl) indenyl)-zirconium dichloride
dimethylsilanediylbis(2-methyl-4-(4'-ethylphenyl)indenyl)-zirconium dichloride
dimethylsilanediylbis(2-methyl-4-(4'-n-propylphenyl) indenyl)-zirconium dichloride
dimethylsilanediylbis(2-methyl-4-(4'-isopropylphenyl) indenyl) zirconium dichloride
dimethylsilanediylbis(2-methyl-4-(4'-n-butylphenyl) indenyl)-zirconium dichloride dimethylsilanediylbis(2-methyl-4-(4'-hexylphenyl indenyl)-zirconium dichloride
dimethylsilanediylbis(2-methyl-4-(4'-sec-butylphenyl) indenyl)-zirconium dichloride
dimethylsilanediylbis(2-ethyl-4-phenyl)indenyl)zirconium dichloride
dimethylsilanediylbis(2-ethyl-4-(4'-methylphenyl)indenyl)-zirconium dichloride
dimethylsilanediylbis(2-ethyl-4-(4'-ethylphenyl)indenyl) zirconium dichloride
dimethylsilanediylbis(2-ethyl-4-(4'-n-propylphenyl) indenyl)-zirconium dichloride
dimethylsilanediylbis(2-ethyl-4-(4'-isopropylphenyl) indenyl)-zirconium dichloride
dimethylsilanediylbis(2-ethyl-4-(4'-n-butylphenyl)indenyl)-zirconium dichloride
dimethylsilanediylbis(2-ethyl-4-(4'-hexylphenyl)indenyl) zirconium dichloride
dimethylsilanediylbis(2-ethyl-4-(4'-pentylphenyl)indenyl)-zirconium dichloride
dimethylsilanediylbis(2-ethyl-4-(4'-cyclohexylphenyl) indenyl)-zirconium dichloride
dimethylsilanediylbis(2-ethyl-4-(4'-sec-butylphenyl) indenyl)-zirconium dichloride
dimethylsilanediylbis(2-ethyl-4-(41'-tert-butylphenyl) indenyl)-zirconium dichloride
dimethylsilanediylbis(2-ethyl-4-(3',5'-di-tert-butylphenyl)-indenyl)zirconium dichloride
methylidenebis(2-ethyl-4-(4'-tert-butylphenyl)indenyl) zirconium dichloride
isopropylidenebis(2-ethyl-4-(4'-tert-butylphenyl)indenyl)-zirconium dichloride
5 dimethylsilanediylbis(2-n-propyl-4-phenyl)indenyl) zirconium dichloride
dimethylsilanediylbis(2-n-propyl-4-(4'-methylphenyl) indenyl)-zirconium dichloride
dimethylsilanediylbis(2-n-propyl-4-(4'-ethylphenyl) indenyl)-zirconium dichloride
dimethylsilanediylbis(2-n-propyl-4-(4'-n-propylphenyl) indenyl)-zirconium dichloride
dimethylsilanediylbis(2-n-propyl-4-(4'-isopropylphenyl) indenyl)-zirconium dichloride
dimethylsilanediylbis(2-n-propyl-4-(4'-n-butylphenyl) indenyl)-zirconium dichloride
dimethylsilanediylbis(2-n-propyl-4-(4'-hexylphenyl) indenyl)-zirconium dichloride
dimethylsilanediylbis(2-n-propyl-4-(4'-cyclohexylphenyl) indenyl)-zirconium dichloride
dimethylsilanediylbis(2-n-propyl-4-(4'-sec-butylphenyl) indenyl)-zirconium dichloride
dimethylsilanediylbis(2-n-propyl-4-(4'-tert-butylphenyl) indenyl)-zirconium dichloride
dimethylsilanediylbis(2-n-propyl-4-(31,5'-di-tert-butylphenyl)-indenyl)zirconium dichloride
methylidenebis(2-n-propyl-4-(4'-tert-butylphenyl)indenyl)-zirconium dichloride
isopropylidenebis(2-n-propyl-4-(4'-tert-butylphenyl) indenyl)-zirconium dichloride
dimethylsilanediylbis(2-n-butyl-4-phenyl)indenyl) zirconium dichloride
dimethylsilanediylbis(2-n-butyl-4-(4'-methylphenyl) indenyl)-zirconium dichloride
dimethylsilanediylbis(2-n-butyl-4-(4'-ethylphenyl)indenyl)-zirconium dichloride
dimethylsilanediylbis(2-n-butyl-4-(4'-n-propylphenyl indenyl)-zirconium dichloride
dimethylsilanediylbis(2-n-butyl-4-(4'-isopropylphenyl) indenyl)-zirconium dichloride
dimethylsilanediylbis(2-n-butyl-4-(4'-n-butylphenyl) indenyl)-zirconium dichloride
dimethylsilanediylbis(2-n-butyl-4-(4'-hexylphenyl) indenyl)-zirconium dichloride
dimethylsilanediylbis(2-n-butyl-4-(4'-cyclohexylphenyl) indenyl)-zirconium dichloride
dimethylsilanediylbis(2-n-butyl-4-(4'-sec-butylphenyl) indenyl)-zirconium dichloride
dimethylsilanediylbis(2-n-butyl-4-(4'-tert-butylphenyl) indenyl)-zirconium dichloride
dimethylsilanediylbis(2-hexyl-4-phenyl)indenyl)zirconium dichloride
dimethylsilanediylbis(2-hexyl-4-(4'-methylphenyl) indenyl)-zirconium dichloride
dimethylsilanediylbis(2-hexyl-4-(4'-ethylphenyl)indenyl) zirconium dichloride
dimethylsilanediylbis(2-hexyl-4-(4'-n-propyl-phenyl)-indenyl)-zirconium dichloride
Dimethylsilanediylbis(2-hexyl-4-(4'-isopropylphenyl) indenyl)-zirconium dichloride
dimethylsilanediylbis(2-hexyl-4-(4'-n-butylphenyl) indenyl)-zirconium dichloride
dimethylsilanediylbis(2-hexyl-4-(4'-hexylphenyl)indenyl) zirconium dichloride
dimethylsilanediylbis(2-hexyl-4-(4'-cyclohexylphenyl) indenyl)-zirconium dichloride
dimethylsilanediylbis(2-hexyl-4-(4'-sec-butylphenyl) indenyl)-zirconium dichloride
dimethylsilanediylbis(2-hexyl-4-(4'-tert-butylphenyl) indenyl)-zirconium dichloride
dimethylgermandiylbis(2-ethyl-4-(4'-tert-butylphenyl) indenyl)-zirconium dichloride
dimethylgermandiylbis(2-methyl-4-(4'-tert-butylphenyl) indenyl)-zirconium dichloride
ethylidenebis(2-ethyl-4-phenyl)indenyl)zirconium dichloride
ethylidenebis(2-ethyl-4-(4'-tert-butylphenyl)indenyl) zirconium dichloride
ethylidenebis(2-n-propyl-4-(4'-tert-butylphenyl)indenyl) zirconium dichloride
ethylidenebis(2-methyl-4-(4'-tert-butylphenyl)indenyl) zirconium dichloride
methylethylidenebis(2-ethyl-4-(4'-tert-butylphenyl) indenyl)-zirconium dichloride
dimethylsilanediyl(2-methylazapentalene)(2-methylindenyl)-zirconium dichloride
dimethylsilanediyl(2-methylazapentalene)(2-methyl-4-phenylindenyl)zirconium dichloride
dimethylsilanediyl(2-methylazapentalene)(2-methyl-4,5-benzoindenyl)zirconium dichloride
dimethylsilanediyl(2-methylazapentalene)(2-ethyl-4-(4'-tert-butylphenylindenyl)zirconium dichloride
dimethylsilanediyl(2-methylazapentalene)(2-methyl-4-(4'-tert-butylphenyl)indenyl)zirconium dichloride
dimethylsilanediyl(2-methylazapentalene)(2-n-propyl-4-(4'-tert-butylphenyl)indenyl)zirconium dichloride
dimethylsilanediyl(2-ethylazapentalene)(2-methyl-4-phenylindenyl)zirconium dichloride
5 dimethylsilanediyl(2-ethylazapentalene)(2-methyl-4-phenylindenyl)zirconium dichloride
dimethylsilanediyl(2-ethylazapentalene)(2-methyl-4,5-benzoindenyl)zirconium dichloride
dimethylsilanediyl(2-ethylazapentalene)(2-ethyl-4-(4'-tert-butylphenylindenyl)zirconium dichloride
dimethylsilanediyl(2-ethylazapentalene)(2-methyl-4-(4'-tert-butylphenyl)indenyl)zirconium dichloride
Dimethylsilanediyl(2-ethylazapentalene)(2-n-propyl-4-(4'-tert-butylphenyl)indenyl)zirconium dichloride 15 dimethylsilanediyl(2-methylthiapentalene)(2-methylindenyl)-zirconium dichloride dimethylsilanediyl(2-methylthiapentalene)(2-methyl-4-phenylindenyl)zirconium dichloride dimethylsilanediyl(2-methylthiapentalene)(2-methyl-4,5-benzoindenyl)zirconium dichloride dimethylsilanediyl(2-methylthiapentalene)(2-ethyl-4-(4-tert-butylphenyl)indenyl)zirconium dichloride dimethylsilanediyl(2-methylthiapentalene)(2-n-propyl-4-(4'-tert-butylphenyl)indenyl)zirconium dichloride dimethylsilanediyl(2-ethylthiapentalene)(2-methylindenyl)-zirconium dichloride dimethylsilanediyl(2-ethylthiapentalene)(2-methyl-4-phenylindenyl)zirconium dichloride dimethylsilanediyl(2-ethylthiapentalene)(2-methyl-4,5-benzoindenyl)zirconium dichloride dimethylsilanediyl(2-ethylthiapentalene)(2-ethyl-4-(4'-tert-butylphenyl)indenyl)zirconium dichloride dimethylsilanediyl(2-ethylthiapentalene)(2-n-propyl-4-(4'-tert-butylphenyl)indenyl)zirconium dichloride In the purification process of the present invention, at least one metallocene halide of the formula (Ia) or (IIa) is reacted with at least one ligand exchange component $M^1YR^3$, forming the metallocenes of the formula (I) or (II). Here, the ligand exchange component serves to introduce the ligand $Y—R^3$. The metallocenes of the formula (I) and (II) can, owing to their good solubility, be obtained in the required quality and in good space-time yields by crystallization. The salts formed in the ligand exchange can, for example, be removed by known filtration techniques.

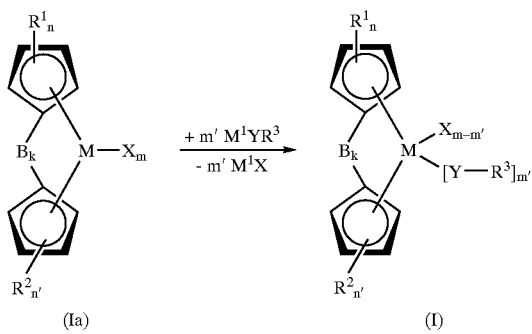

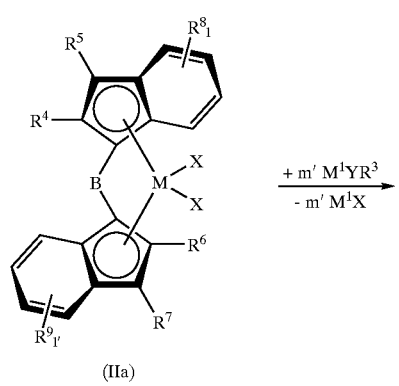

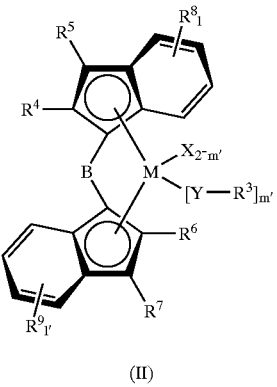

(II)

Here, $M^1$ is a cation or a cationic fragment such as Li, Na, K, MgCl, MgBr, MgI or the ammonium cation corresponding to an amine, and the other radicals are as defined above.

The replacement of the halide ligands in metallocene halides by other ligands is known in principle. In particular, the replacement of chloride ligands by other anions which can act as ligands on the zirconocene has been described (e.g. Replacement of chloride by aryloxide: T. Repo et al., J. Organomet. Chem. 541 (1997), 363, and references cited therein; B. Khera et al., Polyhedron 3 (5), (1984), 611, and references cited therein; B. Khera et al., Polyhedron 2 (11), (1983), 1177; Replacement of chloride by alkyl or aryl: E. W. Abel, F. G. Stone, G. Wilkinson, Comprehensive Organometallic Chemistry II, Volume 4, Elsevier Science Ltd., p. 573, 575, 577; Replacement of chloride by carboxylate: E. W. Abel, F. G. Stone, G. Wilkinson, Comprehensive Organometallic Chemistry II, Volume 4, Elsevier Science Ltd., p. 525; Replacement of chloride by various further anions: E. W. Abel, F. G. Stone, G. Wilkinson, Comprehensive Organometallic Chemistry II, Volume 4, Elsevier Science Ltd., chapter 5, 10 and 11).

In the purification process of the present invention, metallocene halides are firstly reacted with salts of the formula $M^1—Y—R^3$ in an inert solvent or solvent mixture at from 0° C. to +200° C., preferably from 40° C. to 140° C., particularly preferably from 60° C. to 110° C.

The compound $M^1—Y—R^3$ used in the purification process of the present invention can be prepared, for example, by deprotonation of the acid compound $H—Y—R^3$ using a suitable base, for example butyllithium, methyllithium, sodium hydride, potassium hydride, sodium, potassium, Grignard compounds or amines, in an inert solvent or solvent mixture, or $M^1—Y—R^3$ is a commercially available organometallic compound such as an organolithium compound, for example methyllithium, an organoaluminum compound, for example trimethylaluminum, or a Grignard compound, for example benzylmagnesium chloride.

Nonlimiting examples of suitable solvents are hydrocarbons which may be halogenated, e.g. benzene, toluene, xylene, mesitylene, ethylbenzene, chlorobenzene, dichlorobenzene, fluorobenzene, decalin, tetralin, pentane, hexane, cyclohexane, ethers such as diethyl ether, di-n-butyl ether, tert-butyl methyl ether (MTBE), tetrahydrofuran (THF), 1,2-dimethoxyethane (DME), anisole, triglyme, dioxane, amides such as dimethylformamide (DMF), dimethylacetamide, N-methyl-2-pyrrolidinone (NMP), sulfoxides such as dimethyl sulfoxide (DMSO), phosphoramides such as hexamethylphosphoramide, urea derivatives such as 1,3-dimethyltetrahydro-2(1H)-pyrimidinone, ketones such as acetone, ethyl methyl ketone, esters such as ethyl acetate, nitriles such as acetonitrile and also any mixtures of these. Preference is given to solvents or solvent mixtures in which the subsequent reaction with the metallocene dichloride can likewise be carried out. Nonlimiting examples of such solvents are toluene, hexane, heptane, xylene, tetrahydrofuran (THF), dimethoxyethane (DME), toluene/THF, heptane/DME and toluene/DME.

The compounds of the type H—Y—$R^3$ are, for example, alcohols, phenols, carboxylic acids, alkylsulfonic and arylsulfonic acids, primary and seconary amines, primary and secondary anilines, carboxamides, sulfonamides, dialkylphosphines or diarylphosphines and dialkylphosphine oxides or diarylphosphine oxides. Examples of CH-acid, enolisable compounds H—Y—$R^3$ are malonic esters, cyanoacetic esters, acetoacetic esters, 1,3-diketones, enolisable esters and enolisable ketones.

Compounds of the type H—Y—$R^3$ preferably contain only one functional group H—Y and the radical $R^3$ is as defined above.

Illustrative but nonlimiting examples of compounds of the formula H—Y—$R^3$ which can be used according to the present invention are:

2,4-di-tert-butylphenol; 2,6-di-tert-butylphenol; 3,5-di-tert-butylphenol; 2,6-di-sec-butylphenol; 2,4-dimethylphenol; 2,3-dimethylphenol; 2,5-dimethylphenol; 2,6-dimethylphenol; 3,4-dimethylphenol; 3,5-dimethylphenol; phenol; 2-methylphenol; 3-methylphenol; 4-methylphenol; 2-ethylphenol; 3-ethylphenol; 4-ethylphenol; 2-sec-butylphenol; 2-tert-butylphenol; 3-tert-butylphenol; 4-sec-butylphenol; 4-tert-butylphenol; 2-isopropyl-5-methylphenol; 4-isopropyl-3-methylphenol; 5-isopropyl-2-methylphenol; 5-isopropyl-3-methylphenol; 2,4-bis, (2-methyl-2-butyl)phenol; 2,6-di-tert-butyl-4-methylphenol; 4-nonylphenol;

2-isopropylphenol; 3-isopropylphenol; 4-isopropylphenol; 2-propylphenol; 4-propylphenol; 2,3,5-trimethylphenol; 2,3,6-trimethylphenol; 2,4,6-trimethylphenol; 3,4,5-trimethylphenol; 2-tert-butyl-4-methylphenol; 2-tert-butyl-5-methylphenol; 2-tert-butyl-6-methylphenol; 4-(2-methyl-2-butyl)phenol; 2-tert-butyl-4-ethylphenol; 2,6-diisopropylphenol; 4-octylphenol; 4-(1,1,3,3-tetramethylbutyl)phenol; 2,6-di-tert-butyl-4-ethylphenol; 4-sec-butyl-2,6-di-tert-butylphenol; 4-dodecylphenol; 2,4,6-tri-tert-butylphenol; 3-(pentadecyl)phenol; 2-methyl-1-naphthol;

1-naphthol; 2-naphthol; 1-acenaphthenol; 2-hydroxybiphenyl; 3-hydroxybiphenyl; 4-hydroxybiphenyl; hydroxypyridines; hydroxyquinolines; 2-hydroxycarbazole; hydroxyquinaldines; 8-hydroxyquinazoline; 2-hydroxyquinoxaline; 2-hydroxydibenzofuran; 2-hydroxydiphenylmethane, 1-hydroxyisoquinolines, 5,6,7,8-tetrahydro-1-naphthol; methanol; ethanol; propanol; isopropanol; butanol; tert-butanol; isobutanol; 2-butanol; hexanol; cyclohexanol; octadecanol; benzyl alcohol; 2-methylbenzyl alcohol; 3-methylbenzyl alcohol; 4-methylbenzyl alcohol; aniline; N-methylaniline; o-toluidine; 2,3-dimethylaniline; 2,4-dimethylaniline; 2,5-dimethylaniline; 2,6-dimethylaniline; N-ethylaniline; 2-ethylaniline; N-ethyl-o-toluidine; N-ethyl-m-toluidine; 2-isopropylaniline; 2-propylaniline; 2,4,6-trimethylaniline; 2-tert-butylaniline; 2,3-dimethyl-N-ethylaniline; isopropylamine; tert-butylamine; diethylamine; N-methylisopropylamine; N-ethylisopropylamine; diisopropylamine; N-methyl-tert-butylamine; N-benzylmethylamine; 2-methylbenzylamine; 3-methylbenzylamine; 4-methylbenzylamine; 1-phenylethylamine; 2-phenylethylamine; acetic acid; propionic acid; butyric acid; phenylacetic acid; benzoic acid; toluic acid; dimethylbenzoic acid; 4-tert-butylbenzoic acid; methanesulfonic acid; trifluoromethanesulfonic acid; p-toluenesulfonic acid; N-methylacetamide; N-methylpropionamide; benzamide; diphenylphosphine; dimethyl malonate; diethyl malonate; dimethyl methylmalonate; diethyl methylmalonate; diethyl ethylmalonate; methyl acetoacetate; ethyl acetoacetate; ethyl 2-ethylacetoacetate; 1,3-pentanedione; dibenzoylmethane; methyl phenylacetate; methyl isobutyrate; acetophenone; tert-butyl methyl ketone and phenylacetone.

The molar ratio of reagent $M^1$—Y—$R^3$ to the metallocene halide, in particular the metallocene dichloride (e.g. of the formula III) is generally in the range from 5:1 to 0.8:1, preferably from 2.5:1 to 0.91.

The concentration of metallocene dichloride (e.g. of the formula IIa) or of reagent $M^1$—Y—$R^3$ in the reaction mixture is generally in the range from 0.001 mol/l to 8 mol/l, preferably from 0.01 to 3 mol/l, particularly preferably from 0.05 mol/l to 2 mol/l.

The reaction time for the reaction of the metallocene dichloride (e.g. of the formula IIa) with the reagent $M^1$—Y—$R^3$ is generally in the range from 5 minutes to 1 week, preferably from 15 minutes to 48 hours.

After conversion of the metallocenes of the formulae (Ia) and (IIa) into the metallocenes of the formulae (I) and (II), insoluble constituents such as the salts or metal oxyhalides formed are preferably separated off before the new metallocenes are crystallized. For this purpose preference is given to filtering and extracting a solution or suspension of the new metallocenes in the inert solvent or solvent mixture which has been used in the ligand exchange reaction. The recrystallization is preferably carried out in aprotic hydrocarbons, in particular polar aprotic hydrocarbons. Particular preference is given to toluene, hexane, heptane, xylene, tetrahydrofuran (THF), dimethoxyethane (DME), toluene/THF, heptane/DME or toluene/DME.

The solvent or solvent mixture used in the extraction is at a temperature in the range from 20° C. to the boiling point of the solvent or solvent mixture. The extraction is preferably carried out at 0–20° C. below the boiling point.

The resulting solution of the new metallocene is possibly concentrated by evaporation and the new metallocene subsequently crystallizes out.

The crystallization is carried out at from −78° C. to 200° C., preferably from −30° C. to 110° C., particularly preferably from −15° C. to 30° C.

The purified metallocene obtained by crystallization can in turn be isolated from the mother liquor by filtration techniques.

The process of the present invention enables at least twice as much metallocene to be purified in existing apparatuses as was possible hitherto. In preferred embodiments, this factor is substantially exceeded, so that costly capacity expansions can be avoided.

The metallocenes of the formulae I and II obtainable by the purification process of the present invention are highly active catalyst components for olefin polymerization. Depending on the substitution pattern of the ligands, the metallocenes can be obtained as an isomer mixture. For the polymerization, the metallocenes are preferably used as pure isomers.

Preference is given to using the pseudo-rac metallocenes of the formula II.

The metallocenes of the formulae I and II obtainable by the purification process of the present invention are particularly suitable as constituents of catalyst systems for preparing polyolefins by polymerization of at least one olefin in the presence of a catalyst comprising at least one cocatalyst and at least one metallocene. For the purposes of the present invention, the term polymerization encompasses both homopolymerization and copolymerization.

The metallocenes of the formulae I and II, in particular of the formula II, obtainable by the purification process of the present invention can be used for the polymerization of one or more olefins of the formula $R^\alpha$—CH=CH—$R^\beta$, where $R^\alpha$ and $R^\beta$ are identical or different and are each a hydrogen atom or a hydrocarbon radical having from 1 to 20 carbon atoms, in particular from 1 to 10 carbon atoms, and $R^\alpha$ and $R_\beta$ together with the atoms connecting them may form one or more rings. Examples of such olefins are 1-olefins having 2–40, preferably from 2 to 10, carbon atoms, e.g. ethene, propene, 1-butene, 1-pentene, 1-hexene, 4-methyl-1-pentene or 1-octene, styrene, dienes such as 1,3-butadiene, 1,4-hexadiene, vinylnorbornene, norbornadiene, ethylnorbornadiene and cyclic olefins such as norbornene, tetracyclododecene or methylnorbornene. Preference is given to homopolymerizing ethylene or propylene or copolymerizing ethylene with one or more cyclic olefins such as norbornene and/or one or more dienes having from 4 to 20 carbon atoms, e.g. 1,3-butadiene or 1,4-hexadiene. Examples of such copolymers are ethylene-norbornene copolymers, ethylene-propylene copolymers and ethylene-propylene-1,4-hexadiene copolymers.

The metallocenes of the formulae I and II obtained in the purification process of the present invention display olefin polymerization activities which are at least equal to and sometimes superior to those of the dihalide compounds, and the polyolefins obtained display a reduction in the proportion of undesirable low molecular weight extractables.

The polymerization is carried out at from −60 to 300° C. preferably from 50 to 200° C., very particularly preferably from 50–80° C. The pressure is from 0.5 to 2000 bar, preferably from 5 to 64 bar.

The polymerization can be carried out in solution, in bulk, in suspension or in the gas phase, continuously or batchwise, in one or more stages. Preferred embodiments are gas-phase and bulk polymerization.

The catalyst used preferably comprises one of the metallocene compounds obtainable by the purification process of the present invention. It is also possible to use mixtures of two or more metallocene compounds, e.g. for preparing polyolefins having a broad or multimodal molar mass distribution.

The cocatalyst, which together with a metallocene of the formula I or II obtainable by the purification process of the present invention forms the catalyst system, comprises at least one compound such as an aluminoxane or a Lewis acid or an ionic compound which reacts with a metallocene to convert it into a cationic compound.

As aluminoxane, preference is given to using a compound of the formula (VII)

$(RAlO)_n$        (VII).

Further suitable aluminoxanes may be, for example, cyclic as in formula (VI)

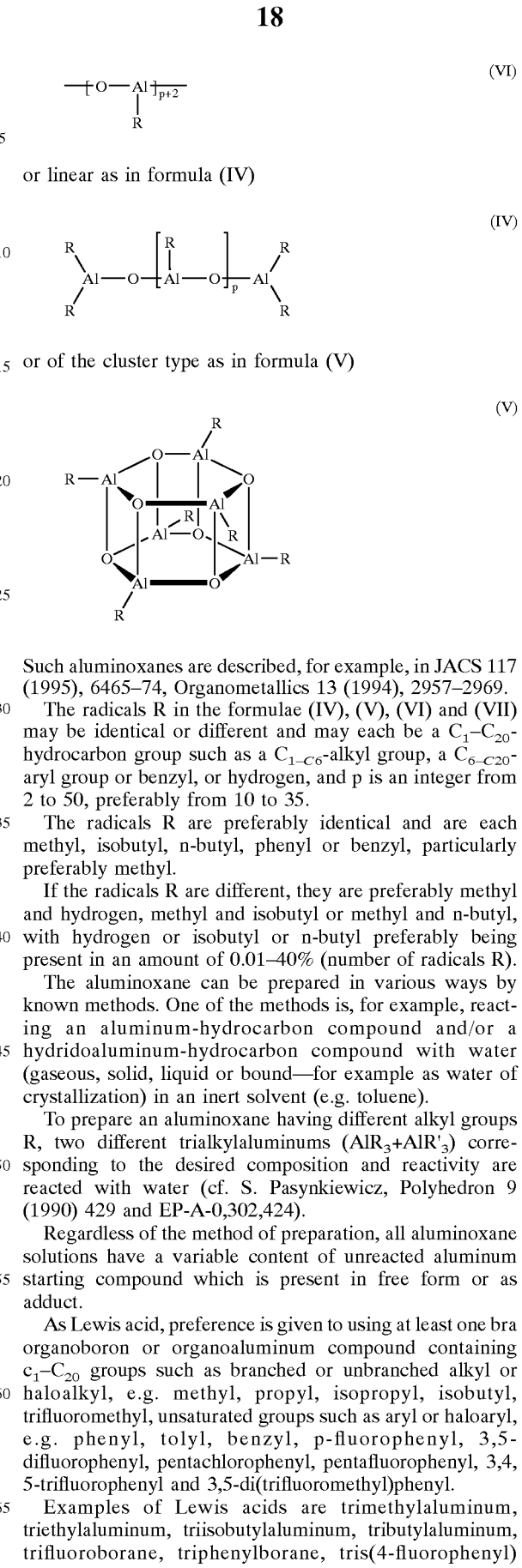

or linear as in formula (IV)

or of the cluster type as in formula (V)

Such aluminoxanes are described, for example, in JACS 117 (1995), 6465–74, Organometallics 13 (1994), 2957–2969.

The radicals R in the formulae (IV), (V), (VI) and (VII) may be identical or different and may each be a $C_1$–$C_{20}$-hydrocarbon group such as a $C_1$–$C_6$-alkyl group, a $C_6$–$C_{20}$-aryl group or benzyl, or hydrogen, and p is an integer from 2 to 50, preferably from 10 to 35.

The radicals R are preferably identical and are each methyl, isobutyl, n-butyl, phenyl or benzyl, particularly preferably methyl.

If the radicals R are different, they are preferably methyl and hydrogen, methyl and isobutyl or methyl and n-butyl, with hydrogen or isobutyl or n-butyl preferably being present in an amount of 0.01–40% (number of radicals R).

The aluminoxane can be prepared in various ways by known methods. One of the methods is, for example, reacting an aluminum-hydrocarbon compound and/or a hydridoaluminum-hydrocarbon compound with water (gaseous, solid, liquid or bound—for example as water of crystallization) in an inert solvent (e.g. toluene).

To prepare an aluminoxane having different alkyl groups R, two different trialkylaluminums ($AlR_3 + AlR'_3$) corresponding to the desired composition and reactivity are reacted with water (cf. S. Pasynkiewicz, Polyhedron 9 (1990) 429 and EP-A-0,302,424).

Regardless of the method of preparation, all aluminoxane solutions have a variable content of unreacted aluminum starting compound which is present in free form or as adduct.

As Lewis acid, preference is given to using at least one bra organoboron or organoaluminum compound containing $c_1$–$C_{20}$ groups such as branched or unbranched alkyl or haloalkyl, e.g. methyl, propyl, isopropyl, isobutyl, trifluoromethyl, unsaturated groups such as aryl or haloaryl, e.g. phenyl, tolyl, benzyl, p-fluorophenyl, 3,5-difluorophenyl, pentachlorophenyl, pentafluorophenyl, 3,4,5-trifluorophenyl and 3,5-di(trifluoromethyl)phenyl.

Examples of Lewis acids are trimethylaluminum, triethylaluminum, triisobutylaluminum, tributylaluminum, trifluoroborane, triphenylborane, tris(4-fluorophenyl)

borane, tris(3,5-difluorophenyl)borane, tris(4-fluoromethylphenyl)borane, tris(pentafluorophenyl)borane, tris(tolyl)borane, tris(3,5-dimethylphenyl)borane, tris(3,5-difluorophenyl)borane, [(C$_6$F$_5$)$_2$BO]$_2$Al-Me, [(C$_6$F$_5$)$_2$BO]$_3$Al and/or tris(3,4,5-trifluorophenyl)borane. Particular preference is given to tris(pentafluorophenyl)borane.

As ionic cocatalysts, preference is given to using compounds containing a noncoordinating anion, for example tetrakis(pentafluorophenyl)borates, tetraphenylborates, SbF$_6$—, CF$_3$SO$_3$— or ClO$_4$—. As cationic counterion, use is made of protonated Lewis bases such as methylamine, aniline, dimethylamine, diethylamin, N-methylaniline, diphenylamine, N,N-dimethylaniline, trimethylamine, triethylamine, tri-n-butylamine, methyldiphenylamine, pyridine, p-bromo-N,N-dimethylaniline, p-nitro-N,N-dimethylaniline, triethylphosphine, triphenylphosphine, diphenylphosphine, tetrahydrothiophene or triphenylcarbenium.

Examples of such ionic compounds are
triethylammonium tetra(phenyl)borate,
tributylammonium tetra(phenyl)borate,
trimethylammonium tetra(tolyl)borate,
tributylammonium tetra(tolyl)borate,
tributylammonium tetra(pentafluorophenyl)borate,
tributylammonium tetra(pentafluorophenyl)aluminate,
tripropylammonium tetra(dimethylphenyl)borate,
tributylammonium tetra(trifluoromethylphenyl)borate,
tributylammonium tetra(4-fluorophenyl)borate,
N,N-dimethylanilinium tetra(phenyl)borate,
N,N-diethylanilinium tetra(phenyl)borate,
N,N-dimethylanilinium tetrakis(pentafluorophenyl)borate,
N,N-dimethylanilinium tetrakis(pentafluorophenyl) aluminate,
di(propyl)ammonium tetrakis(pentafluorophenyl)borate,
di(cyclohexyl)ammonium tetrakis(pentafluorophenyl) borate,
triphenylphosphonium tetrakis(phenyl)borate,
triethylphosphonium tetrakis(phenyl borate,
diphenylphosphonium tetrakis(phenyl)borate,
tri(methylphenyl)phosphonium tetrakis(phenyl)borate,
tri(dimethylphenyl)phosphonium tetrakis(phenyl)borate,
triphenylcarbenium tetrakis(pentafluorophenyl)borate,
triphenylcarbenium tetrakis(pentafluorophenyl)aluminate,
triphenylcarbenium tetrakis(phenyl)aluminate,
ferrocenium tetrakis(pentafluorophenyl)borate and/or
ferrocenium tetrakis(pentafluorophenyl)aluminate.

Preference is given to triphenylcarbenium tetrakis(pentafluorophenyl)borate and/or N,N-dimethylanilinium tetrakis(pentafluorophenyl)borate.

It is also possible to use mixtures of at least one Lewis acid and at least one ionic compound.

Further suitable cocatalyst components are borane or carborane compounds such as
7,8-dicarbaundecaborane(13), undecahydrido-7,8-dimethyl-7,8-dicarbaundecaborane, dodecahydrido-1-phenyl-1,3-dicarbanonaborane, tri(butyl)ammonium undecahydrido-8-ethyl-7,9-dicarbaundecaborate, 4-carbanonaborane (14),
bis(tri(butyl)ammonium) nonaborate,
bis(tri(butyl)ammonium)undecaborate,
bis(tri(butyl)ammonium)dodecaborate,
bis(tri(butyl)ammonium) decachlorodecaborate,
tri(butyl)ammonium 1-carbadecaborate,
tri(butyl)ammonium 1-carbadodecaborate,
tri(butyl)ammonium 1-trimethylsilyl-1-carbadecaborate,
tri(butyl)ammonium bis(nonahydrido-1,3-dicarbanonaborato)cobaltate(III),
tri(butyl)ammonium bis(undecahydrido-7,8-dicarbaundecaborato)ferrate(III).

Further cocatalysts which can be used in unsupported or supported form are the compounds specified in EP-A-0924223, DE-A-19622207, EP-A-0601830, EP-A-0824112, EP-A-0824113, WO 99/06414, EP-A-0811627 and DE-A-19804970.

The support component of the catalyst system of the present invention may be any organic or inorganic, inert solid, in particular a porous support such as talc, inorganic oxides and finely divided polymer powders (e.g. polyolefins).

Suitable inorganic oxides may be found among the oxides of elements of groups 2,3,4,5,13,14,15 and 16 of the Periodic Table of the Elements. Examples of oxides preferred as supports include silicon dioxide, aluminum oxide and also mixed oxides of the two elements and corresponding oxide mixtures. Other inorganic oxides which can be used alone or in combination with the above-mentioned preferred oxidic supports are, for example, MgO, ZrO$_2$, TiO$_2$ or B$_2$O$_3$, to name only a few.

The support materials used have a specific surface area in the range from 10 to 1000 m$^2$/g, a pore volume in the range from 0.1 to 5 ml/g and a mean particle size of from 1 to 500 μm. Preference is given to supports having a specific surface area in the range from 50 to 500 m$^2$/g, a pore volume in the range from 0.5 to 3.5 ml/g and a mean particle size in the range from 5 to 350 μm.

Particular preference is given to supports having a specific surface area in the range from 200 to 400 m$^2$/g, a pore volume in the range from 0.8 to 3.0 ml/g and a mean particle size of from 10 to 200 μm.

If the support material used naturally has a low moisture content or residual solvent content, dehydration or drying before use can be omitted. If this is not the case, for example when using silica gel as support material, dehydration or drying is advisable. Thermal dehydration or drying of the support material can be carried out under reduced pressure with simultaneous inert gas blanketing (e.g. nitrogen). The drying temperature is in the range from 100 to 1000° C., preferably from 200 to 800° C. The parameter pressure is not critical in this case. The duration of the drying process can be from 1 to 24 hours. Shorter or longer drying times are possible, provided that equilibrium with the hydroxyl groups on the support surface can be established under the conditions chosen, which normally takes from 4 to 8 hours.

Dehydration or drying of the support material can also be carried out by chemical means, by reacting the adsorbed water and the hydroxyl groups on the surface with suitable passivating agents. Reaction with the passivating reagent enables all or some of the hydroxyl groups to be converted into a form which leads to no adverse interaction with the catalytically active centers. Suitable passivating agents are, for example, silicon halides and silanes, e.g. silicon tetrachloride, chlorotrimethylsilane, dimethylaminotrichlorosilane, or organometallic compounds of aluminum, boron and magnesium, for example trimethylaluminum, triethylaluminum, triisobutylaluminum, triethylborane, dibutylmagnesium. Chemical dehydration or passivation of the support material is carried out, for example, by reacting a suspension of the support material in a suitable solvent with the passivating reagent in pure form or as a solution in a suitable solvent in the absence of air and moisture. Suitable solvents are, for example, aliphatic or aromatic hydrocarbons such as pentane, hexane, heptane, toluene or xylene. Passivation is carried out at from 25° C. to 120° C., preferably from 50 to 70° C. Higher and lower temperatures are possible. The reaction time is from 30 minutes to 20 hours, preferably from 1 to 5 hours. After chemical dehydration is complete, the support material is isolated by filtration under inert conditions, washed one or more times with suitable inert solvents as have been described above and subsequently dried in a stream of inert gas or under reduced pressure.

Organic support materials such as finely divided polyolefin powders (e.g. polyethylene, polypropylene or polystyrene) can also be used and should likewise be freed of adhering moisture, solvent residues or other impurities by means of appropriate purification and drying operations before use.

The catalyst system is prepared by mixing at least one metallocene as rac-meso isomer mixture, at least one cocatalyst and at least one passivated support.

To prepare the supported catalyst system, at least one of the above-described metallocene components obtainable by the purification process of the present invention is brought into contact with at least one cocatalyst component in a suitable solvent, preferably giving a soluble reaction product, an adduct or a mixture.

The composition obtained in this way is then mixed with the dehydrated or passivated support material, the solvent is removed and the resulting supported metallocene catalyst system is dried to ensure that all or most of the solvent is removed from the pores of the support material. The supported catalyst is obtained as a free-flowing powder.

A process for preparing a free-flowing and possibly prepolymerized supported catalyst system comprises the following steps;

a) preparing a metallocene/cocatalyst mixture in a suitable solvent or suspension medium, where the metallocene component is obtainable from the purification process of the present invention and has one of the above-described structures;
b) applying the metallocene/cocatalyst mixture to a porous, preferably inorganic dehydrated support;
c) removing the major part of the solvent from the resulting mixture;
d) isolating the supported catalyst system;
e) if desired, prepolymerizing the supported catalyst system obtained using one or more olefinic monomer(s) to give a prepolymerized supported catalyst system.

Preferred solvents for preparing the metallocene/cocatalyst mixture are hydrocarbons and hydrocarbon mixtures which are liquid at the chosen reaction temperature and in which the individual components preferably dissolve. However, solubility of the individual components is not a prerequisite as long as it is ensured that the reaction product of metallocene and cocatalyst components is soluble in the solvent selected. Examples of suitable solvents include alkanes such as pentane, isopentane, hexane, heptane, octane and nonane; cycloalkanes such as cyclopentane and cyclohexane; and aromatics such as benzene, toluene, ethylbenzene and diethylbenzene. Very particular preference is given to toluene.

The amounts of aluminoxane and metallocene used in the preparation of the supported catalyst system can be varied over a wide range. Preference is given to a molar ratio of aluminum to transition metal in the metallocene of from 10:1 to 1000:1, very particularly preferably from 50:1 to 500:1.

In the case of methylaluminoxane, preference is given to using 30% strength toluene solutions; however, the use of 10% strength solutions is also possible.

For preactivation, the solid metallocene is dissolved in a solution of the aluminoxane in a suitable solvent. It is also possible to dissolve the metallocene separately in a suitable solvent and subsequently to combine this solution with the aluminoxane solution. Preference is given to using toluene.

The preactivation time is from 1 minute to 200 hours.

The preactivation can take place at room temperature (25° C.). The use of higher temperatures can in some cases shorten the preactivation time required and result in an additional increase in the activity. In this case, higher temperature means a range from 50 to 100° C.

The preactivated solution or metallocene/cocatalyst mixture is subsequently combined with an inert support material, usually silica gel, in the form of a dry powder or as a suspension in one of the abovementioned solvents. The support material is preferably used as a powder. The order of addition is immaterial. The preactivated metallocene/cocatalyst solution or metallocene/cocatalyst mixture can be added to the support material or the support material can be introduced into the solution.

The volume of the preactivated solution or metallocene/cocatalyst mixture can exceed 100% of the total pore volume of the support material used or else can be up to 100% of the total pore volume.

The temperature at which the preactivated solution or metallocene/cocatalyst mixture is brought into contact with the support material can vary in the range from 0 to 100° C. However, lower or higher temperatures are also possible.

Subsequently, all or most of the solvent is removed from the supported catalyst system, with the mixture being able to be stirred and also heated if desired. Preference is given to removing both the visible proportion of the solvent and also the proportion in the pores of the support material. The removal of the solvent can be carried out in a conventional way using reduced pressure and/or flushing with inert gas. In the drying process, the mixture can be heated until the free solvent has been removed, which usually takes from 1 to 3 hours at a preferred temperature of from 30 to 60° C. The free solvent is the visible proportion of solvent in the mixture. For the purposes of the present invention, residual solvent is the proportion enclosed in the pores.

As an alternative to complete removal of the solvent, the supported catalyst system can also be dried only to a certain residual solvent content, with the free solvent having been completely removed. The supported catalyst system can subsequently be washed with a low-boiling hydrocarbon such as pentane or hexane and dried again.

After it has been prepared, the supported catalyst system can either be used directly for the polymerization of olefins or be prepolymerized using one or more olefinic monomers prior to use in a polymerization process. The prepolymerization of supported catalyst systems is described, for example, in WO 94/28034.

As additive, a small amount of an olefin, preferably a α-olefin (for example styrene or phenyldimethylvinylsilane) as activity-promoting component, or, for example, an antistatic can be added during or after the preparation of the supported catalyst system.

As antistatic, use is customarily made of a mixture of a metal salt of Medialan acid, a metal salt of anthranilic acid and a polyamine. Such antistatics are described, for example, in EP-A-0,636,636.

The molar ratio of additive to metallocene component (compound (I)) is preferably from 1:1000 to 1000:1, very particularly preferably from 1:20 to 20:1.

The present invention also provides a process for preparing a polyolefin by polymerization of one or more olefins in the presence of the catalyst system comprising at least one transition metal component of the formula I or II which is obtainable by the purification process of the present invention. For the purposes of the present invention, the term polymerization encompasses both homopolymerization and copolymerization.

The metallocenes of the formulae I and II obtained in the purification process of the present invention display olefin polymerization activities which are at least equal to and sometimes superior to those of the dihalide compounds, and the polyolefins obtained display a reduction in the proportion of undesirable low molecular weight extractables.

The catalyst system described here can be used as sole catalyst component for the polymerization of olefins having from 2 to 20 carbon atoms, but is preferably used in combination with at least one alkyl compound of elements of main group I to III of the Periodic Table, e.g. an aluminum alkyl, magnesium alkyl or lithium alkyl or an aluminoxane. The alkyl compound is added to the monomers or the suspension medium and serves to free the monomers of substances which can adversely affect the catalyst activity. The amount of alkyl compound added depends on the quality of the monomers used.

As molar mass regulator and/or to increase the activity, hydrogen is added if required.

In the polymerization, the antistatic can be introduced into the polymerization system either together with or separately from the catalyst system used.

The polymers prepared using the catalyst system comprising at least one of the metallocenes of the formulae I and II obtained in the purification process of the present invention display a uniform particle morphology and contain no fines. No deposits or caked material occur in the polymerization using the catalyst system.

The catalyst system gives polymers such as polypropylene with extraordinarily high stereospecificity and regiospecificity.

The stereospecificity and regiospecificity of polymers, particularly polypropylene, is defined, in particular, by the triad tacticity (TT) and the proportion of 2-1-inserted propene units (RI), which can be determined from the $^{13}$C-NMR spectra.

The $^{13}$C-NMR spectra are measured in a mixture of hexachlorobutadiene and $d_2$-tetrachloroethane at elevated temperature (365 K). All $^{13}$C-NMR spectra of the polypropylene samples measured are calibrated on the basis of the resonance signal of $d_2$-tetrachloroethane ($\delta$=73.81 ppm).

To determine the triad tacticity of the polypropylene, the methyl resonance signals in the $^{13}$C-NMR spectrum from 23 to 16 ppm are examined; cf. J. C. Randall, Polymer Sequence Determination: Carbon-13 NMR Method, Academic Press New York 1978; A. Zambelli, P. Locatelli, G. Bajo, F. A. Bovey, Macromolecules 8 (1975), 687–689; H. N. Cheng, J. A. Ewen, Makromol. Chem. 190 (1989), 1931–1943. Three successive 1-2-inserted propene units whose methyl groups are on the same side in the "Fischer projection" are referred to as mm triads ($\delta$=21.0 ppm to 22.0 ppm). If only the second methyl group of three successive propene units points to the other side, one speaks of an rr triad ($\delta$=19.5 ppm to 20.3 ppm) and if only the third methyl group of the three successive propene units points to the other side, this is referred to as an mr triad ($\delta$=20.3 ppm to 21.0 ppm). The triad tacticity is calculated according to the following formula:

$$TT(\%) = mm/(mm+mr+rr) \cdot 100$$

If a propene unit is inserted inversely into the growing polymer chain, this is referred to as a 2-1 insertion; cf. T. Tsutsui, N. Ishimaru, A. Mizuno, A. Toyota, N. Kashiwa, Polymer 30, (1989), 1350–56. The following structural arrangements are possible:

$$-CH_2-\underset{|}{\overset{CH_3}{CH}}\overset{\alpha,\alpha}{-}CH_2-\underset{|}{\overset{CH_3}{CH}}-\underset{|}{\overset{CH_3}{CH}}\overset{\alpha,\beta}{-}CH_2\overset{\alpha,\beta}{-}CH_2-\underset{|}{\overset{CH_3}{CH}}-CH_2-\underset{|}{\overset{CH_3}{CH}}-$$

$$-CH_2-\underset{|}{\overset{CH_3}{CH}}\overset{\alpha,\alpha}{-}CH_2-\underset{\underset{CH_3}{|}}{\overset{CH_3}{CH}}-CH\overset{\alpha,\beta}{-}CH_2\overset{\alpha,\beta}{-}CH_2-\underset{|}{\overset{CH_3}{CH}}-CH_2-\underset{|}{\overset{CH_3}{CH}}-$$

$$-CH_2-\underset{|}{\overset{CH_3}{CH}}-CH_2-CH_2-CH_2\overset{\alpha,\delta}{-}CH_2-\underset{|}{\overset{CH_3}{CH}}-CH_2-\underset{|}{\overset{CH_3}{CH}}-CH_2-$$

The proportion of 2-1-inserted propene units ($R^1$) can be calculated according to the following formula:

$$RI(\%) = 0.5I\alpha,\beta(I\alpha,\alpha+I\alpha,\beta+I\alpha,\delta) \cdot 100,$$

where $I\alpha,\alpha$ is the sum of the intensities of the resonance signals at $\delta$=41.84, 42.92 and 46.22 ppm, $I\alpha,\beta$ is the sum of the intensities of the resonance signals at $\delta$=30.13, 32.12, 35.11 and 35.57 ppm and $I\alpha,\delta$ is the intensity of the resonance signal at $\delta$=37.08 ppm.

The isotactic polypropylene which has been prepared using the catalyst system has a proportion of 2-1-inserted propene units RI of <0.5% at a triad tacticity TT of >98.0% and a melting point of >153° C., and the $M_w/M_n$ of the polypropylene prepared according to the present invention is from 2.5 to 3.5.

The copolymers which can be prepared using the catalyst system have a significantly higher molar mass than those of the prior art. At the same time, the use of the catalyst system enables such copolymers to be prepared with high productivity at industrially relevant process parameters without deposit formation.

The polymers prepared by the process are particularly useful for producing hard and stiff shaped bodies having a high tensile strength, for example fibers, filaments, injection-molded parts, films, sheets or large hollow bodies (e.g. pipes).

The invention is illustrated by the following nonlimiting examples.

General procedures: preparation and handling of organometallic compounds was carried out in the absence of air and moisture under argon (Schlenk technique or glove box). All solvents required were purged with argon and dried over molecular sieves before use.

EXAMPLE 1

Dimethylsilanediylbis(2-methyl-4,5-benzoindenyl) zirconium Monochloride mono(2,4-di-tert-butylphenoxide) (1)

20.6 g (0.1 mol) of 2,4-di-tert-butylphenol in 200 ml of toluene/20 ml of THF were admixed at room temperature with 37.2 ml (0.1 mol) of a 20% strength solution of butyllithium in toluene. The mixture was stirred for another 1 hour at 60° C. At room temperature, 28.8 g (0.05 mol) of dimethylsilanediyl-bis(2-methyl-4,5-benzoindenyl) zirconium dichloride were added as a solid. The suspension was stirred at 100° C. for 3 hours and subsequently filtered hot through Celite. The filter cake was extracted 3 times with 100 ml each time of toluene (100° C.). After evaporation of the solvent, the yellow solid which had precipitated was filtered off and dried under reduced pressure. This gave 31.1 g (83%) of dimethylsilanediylbis(2-methyl-4,5- benzoindenyl)zirconium monochloride mono(2,4-di-tert-butylphenoxide) (1).

1H-NMR (400 MHz, CDCl$_3$): 8.05 (dd,1H), 7.75 (m, 2H), 7.65 (dd, 1H), 7.60 (1H), 7.5–7.15 (m, 6H), 7.1 (m, 1H), 7.0 (m, 1H), 6.85 (s, 1H), 6.8 (d, 1H), 6.65 (m, 1H), 5.45 (d, 1H), 2.82 (s, 3H), 2.45 (s, 3H), 1.45 (s, 3H), 1.35 (s, 3H), 1.25 (s, 9H), 0.95 (s, 9H).

Solubility Comparison:

50 mg of dimethylsilanediylbis(2-methyl-4,5-benzoindenyl)zirconium dichloride dissolved completely in 240 ml of toluene at room temperature (solubility: about 0.36 mmol/l).

50 mg of the compound (1) dissolved immediately in <5 ml of toluene at room temperature (solubility: >13 mmol/l).

EXAMPLE 1a

Preparation of a Catalyst Using (1) and Polymerization 35.1 mg (0.047 mmol) of (1) were stirred in 2.1 ml of 30% strength MAO solution in toluene (Al/Zr=215) for 60 minutes at room temperature. 2 g of SiO$_2$ (Grace XPO2107, pretreated at 140° C., 10 mbar, 10 hours) were subsequently added and the mixture was stirred for another 10 minutes. The solvent was removed in an oil pump vacuum.

A dry 2 l reactor was flushed firstly with nitrogen and subsequently with propylene and charged with 1.5 l of liquid propylene. 2 ml of TEA (20% strength in Varsol) were added thereto and the mixture was stirred for 15 minutes. The catalyst system prepared above (0.886 g) was subsequently resuspended in 20 ml of heptane and then injected into the reactor and rinsed in with 15 ml of heptane. The reaction mixture was heated to the polymerization temperature of 60° C. and polymerization was carried out for 1 hour. The polymerization was stopped by venting the remaining propylene. The polymer was dried in a vacuum drying oven. This gave 470 g of polypropylene powder. The reactor displayed no deposits on the inner wall or stirrer. The catalyst activity was 0.53 kg of PP/g of catalyst x h.

COMPARATIVE EXAMPLE

Preparation of a Catalyst Using dimethylsilanediylbis(2-methyl-4,5-benzoindenyl) zirconium Dichloride and Polymerization 27.1 mg (0.047 mmol) of dimethylsilanediylbis(2-methyl-4,5-benzoindenyl)zirconium dichloride were stirred in 2.1 ml of 30% strength MAO solution in toluene (Al/Zr=215) for 60 minutes at room temperature. 2 g of SiO$_2$ (Grace XPO2107, pretreated at 140° C., 10 mbar, 10 hours) were subsequently added and the mixture was stirred for another 10 minutes. The solvent was removed in an oil pump vacuum.

A dry 2 l reactor was flushed firstly with nitrogen and subsequently with propylene and charged with 1.5 l of liquid propylene. 2 ml of TEA (20% strength in Varsol) were added thereto and the mixture was stirred for 15 minutes. The catalyst system prepared above (0.897 g) was subsequently resuspended in 20 ml of heptane and then injected into the reactor and rinsed in with 15 ml of heptane. The reaction mixture was heated to the polymerization temperature of 60° C. and polymerization was carried out for 1 hour. The polymerization was stopped by venting the remaining propylene. The polymer was dried in a vacuum drying oven. This gave 410 g of polypropylene powder. The reactor displayed no deposits on the inner wall or stirrer. The catalyst activity was 0.46 kg of PP/g of catalyst x h.

EXAMPLE 2

Dimethylsilanediyl-bis(2-methylindenyl)zirconium Monochloride mono(2,4-di-tert-butylphenoxide) (2)

1.03 g (5 mmol) of 2,4-di-tert-butylphenol in 10 ml of toluene/1 ml of THF were admixed at room temperature with 1.85 ml (5 mmol) of a 20% strength solution of butyllithium in toluene. The mixture was stirred for another 1 hour at 60° C. At room temperature, 1.19 g (2.5 mmol) of dimethylsilanediyl-bis(2-methylindenyl)zirconium dichloride were added as a solid. The suspension was stirred at 60° C. for 2 hours and subsequently filtered hot through Celite. The filter cake was extracted 3 times with 10 ml each time of toluene (60° C.). After evaporation of the solvent, the yellow solid which had precipitated was filtered off and dried under reduced pressure. This gave 0.87 g (53%) of dimethylsilanediylbis(2-methylindenyl)zirconium monochloride mono(2,4-di-tert-butylphenoxide) (2).

1H-NMR (400 MHz, CDCl$_3$): 8.03 (dd,1H, 7.6 (dd, 1H), 7.25–7.2 (m, 2H), 7.15 (m, 1H), 7.1–7.0 (m, 2H), 6.9 (m, 1H), 6.8 (s, 1H), 6.75 (m, 1H), 6.7 (m, 1H), 6.3 (s, 1H), 5.55 (d, 1H), 2.65 (s, 3H), 2.3 (s, 3H), 1.3 (s, 3H), 1.25 (s, 9H), 1.22 (s, 3H), 1.15 (s, 9H).

Solubility Comparison:

50 mg of dimethylsilanediylbis(2-methylindenyl) zirconium dichloride dissolved completely in 50 ml of toluene at room temperature (solubility: about 2.1 mmol/l).

50 mg of the compound (2) dissolved immediately in <5 ml of toluene at room temperature (solubility: >15 mmol/l).

EXAMPLE 3

Dimethylsilanediylbis(2-methyl-4,5-benzoindenyl) zirconium Monochloride mono(2-isopropyl-5-methylphenoxide) (3)

2.7 g (17.4 mmol) of 2-isopropyl-5-methylphenol in 20 ml of toluene/2 ml of THF were admixed at room temperature with 6.5 ml (17.4 mmol) of a 20% strength solution of butyllithium in toluene. The mixture was stirred for another 1 hour at 60° C. At room temperature, 5.0 g (8.7 mmol) of dimethylsilanediylbis(2-methyl-4,5-benzoindenyl) zirconium dichloride were added as a solid. The suspension was stirred at 100° C. for 4 hours and subsequently filtered hot through Celite. The filter cake was extracted twice with 25 ml each time of toluene (100° C.). After evaporation of the solvent, the yellow solid which had precipitated was filtered off and dried under reduced pressure. This gave 2.5 g (41%) of dimethylsilanediylbis(2-methyl-4,5-benzoindenyl)zirconium monochloride mono(2-isopropyl-5-methylphenoxide) (3).

1H-NMR (400 MHz, CDCl$_3$): 7.9 (dd,1H), 7.81 (m, 1H), 7.74 (m, 1H), 7.54 (m, 2H), 7.45–7.08 (m, 8H), 6.65 (d, 1H), 6.55 (s, 1H), 6.35 (m, 1H), 5.56 (d, 1H), 2.58 (s, 3H), 2.35 (s, 3H), 2.3 (m, 1H), 2.1 (s, 3H), 1.37 (s, 3H), 1.27 (s, 3H), 0.75 (d, 3H), 0.62 (d, 3H).

Solubility Comparison:

50 mg of dimethylsilanediylbis(2-methyl-4,5-benzoindenyl)zirconium dichloride dissolved completely in 240 ml of toluene at room temperature (solubility: about 0.36 mmol/l).

50 mg of the compound (3) dissolved in 4 ml of toluene at room temperature (solubility: about 18 mmol/l).

EXAMPLE 4

Dimethylsilanediylbis(2-methylindenyl)zirconium Monochloride mono(2-isopropyl-5-methylphenoxide) (4)

3.2 g (21 mmol) of 2-isopropyl-5-methylphenol in 20 ml of toluene/2 ml of THF were admixed at room temperature with 7.8 ml (21 mmol) of a 20% strength solution of butyllithium in toluene. The mixture was stirred for another 1 hour at 60° C. At room temperature, 5.0 g (10.5 mmol) of dimethylsilanediylbis(2-methylindenyl)zirconium dichloride were added as a solid. The suspension was stirred at 100° C. for 2 hours and subsequently filtered hot through Celite. The filter cake was extracted twice with 25 ml each time of toluene (100° C.). After evaporation of the solvent, the yellow solid which had precipitated was filtered off and dried under reduced pressure. This gave 1.36 g (22%) of dimethylsilanediylbis(2-methylindenyl)zirconium monochloride mono(2-isopropyl-5-methylphenoxide) (4).

1H-NMR (400 MHz, CDCl$_3$): 8.0 (m, 1H), 7.81 (m, 1H), 7.3–6.8 (m, 8H), 6.55 (dm, 1H), 6.1 (s, 1H), 5.9 (d, 1H), 2.7 (hept, 1H), 2.45 (s, 3H), 2.25 (s, 3H), 2.18 (s, 3H), 1.4 (s, 3H), 1.25 (s, 3H), 1.1 (d, 3H), 0.95 (d, 3H).

Solubility Comparison:

50 mg of dimethylsilanediylbis(2-methylindenyl)zirconium dichloride dissolved completely in 50 ml of toluene at room temperature (solubility: about 2.1 mmol/l).

50 mg of the compound (4) dissolved in 5 ml of toluene at room temperature (solubility: about 17 mmol/l).

EXAMPLE 5

Dimethylsilanediylbis(2-methylindenyl)zirconium Monochloride mono(2,4-dimethylphenoxide) (5)

1.0 g (8.2 mmol) of 2,4-dimethylphenol in 20 ml of toluene/2 ml of THF were admixed at room temperature with 3.0 ml (8.2 mmol) of a 20% strength solution of butyllithium in toluene. The mixture was stirred for another 1 hour at 60° C. At room temperature, 1.9 g (4.0 mmol) of dimethylsilanediylbis(2-methylindenyl)zirconium dichloride were added as a solid. The suspension was stirred at 60° C. for 8 hours and subsequently filtered hot through Celite. After evaporation of the solvent to about 7 ml, the yellow solid which had precipitated at −30° C. was filtered off and dried under reduced pressure. This gave 0.65 g (29%) of dimethylsilanediylbis(2-methylindenyl)zirconium monochloride mono(2,4-dimethylphenoxide) (5).

1H-NMR (400 MHz, CDCl$_3$): 7.96 (dd, 1H), 7.6 (m, 1H), 7.36 (m, 1H), 7.31 (m, 1H), 7.29 (d, 1H), 7.1 (m, 1H), 6.99 (m, 1H), 6.94 (m, 1H), 6.88 (s, 1H), 6.75 (m, 1H), 6.65 (m, 1H), 6.06 (s, 1H), 5.93 (d, 1H), 2.4 (s, 3H), 2.24 (s, 3H), 2.18 (s, 3H), 1.85 (s, 3H), 1.35 (s, 3H), 1.24 (s, 3H).

EXAMPLE 6

Dimethylsilanediylbis(2-methyl-4,5-benzoindenyl)zirconium Monochloride mono(2,4-di-tert-pentylphenoxide) (6)

0.85 g (3.5 mmol) of 2,4-di-tert-pentylphenol in 10 ml of toluene/1 ml of THF were admixed at room temperature with 1.3 ml (3.5 mmol) of a 20% strength solution of butyllithium in toluene. The mixture was stirred for another: 1 hour at 60° C. At room temperature, 1.0 g (1.74 mmol) of dimethylsilanediylbis(2-methyl-4,5-benzoindenyl)zirconium dichloride were added as a solid. The suspension was stirred at 100° C. for 4 hours, diluted with 40 ml of toluene and subsequently filtered hot through Celite. The filter cake was extracted twice with 25 ml each time of toluene (100° C.). After evaporation of the solvent to, 10 ml, the yellow solid which had precipitated was filtered off, washed with a little cold toluene and dried under reduced pressure. This gave 0.85 g (63%) of dimethylsilanediylbis(2-methyl-4,5-benzoindenyl)zirconium monochloride mono(2,4-di-tert-pentylphenoxide) (6).

1H-NMR (400 MHz, CDCl$_3$): 8.00 (d, 1H) 7.74 (t, 2H), 7.64–7.57 (m, 2H), 7.45–7.27 (m, 5H), 7.14 (s, 1H), 7.10 (m, 1H), 6.98 (m, 1H), 6.78 (s, 1H), 6.65 (d, 1H), 6.52 (dd, 1H), 5.38 (d, 1H), 2.78 (s, 3H), 2.41 (s, 3H), 1.46 (quart., 2H), 1.41 (s, 3H), 1.30 (S, 3H), 1.22 (m, 2H), 1.14 (s, 3H), 1.13 (s, 3H), 0.91 (s, 3H), 0.88 (s, 3H), 0.57 (t, 3H), 0.39 (t, 3H).

Solubility Comparison:

50 mg of dimethylsilanediylbis(2-methyl-4,5-benzoindenyl)zirconium dichloride dissolved completely in 240 ml of toluene at room temperature (solubility: about 0.36 mmol/l).

55 mg of the compound (6) dissolved in 4 ml of toluene at room temperature (solubility: about 17.7 mmol/l).

We claim:

1. A process for converting a bridged metallocene of formula (IIa)

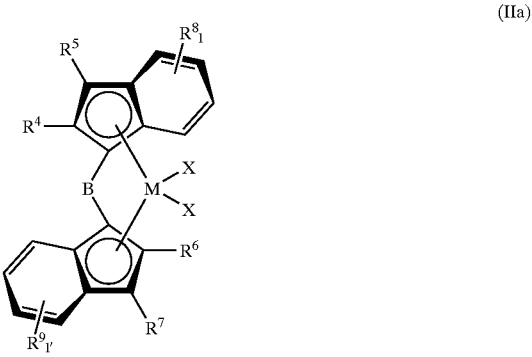

(IIa)

where

M is Ti, Zr or Hf, $R^4$, $R^6$ are identical or different and are each hydrogen or a $C_1$–$C_{20}$ group, $R^5$, $R^7$ are identical or different and are each a hydrogen atom or a $C_1$–$C_{20}$ group, $R^8$, $R^9$ are identical or different and are each a hydrogen atom, a halogen atom or a $C_1$–$C_{30}$ group, and two radicals $R^8$ and $R^9$ may form a monocyclic or polycyclic ring system which may in turn be substituted, l, l' are identical or different and are each an integer from zero to 4, X is a halogen atom, and B is a bridging structural element between the two indenyl radicals, to a bridged metallocene of formula (II),

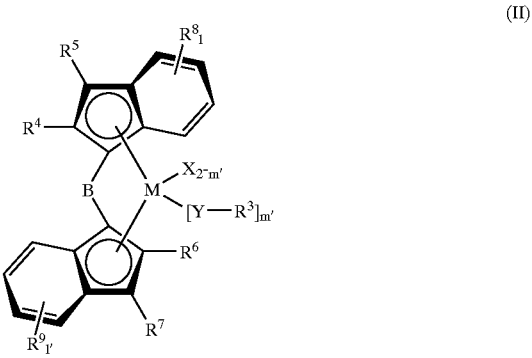

(II)

where

M, X, l, l', B, $R^4$, $R^5$, $R^6$, $R^7$, $R^8$ and $R^9$ have the same meaning as above, Y is an element of main group VI of the Periodic Table of the Elements, m' is 1 or 2, and $R^3$ are identical or different and are each halogen or a $C_1$–$C_{30}$ group;

comprising the steps a) reacting a bridged metallocene of the formula (IIa) with a ligand exchange component $M^1YR^3$ where Y and $R^3$ are as defined above, $M^1$ is a cation, a cationic fragment, or an ammonium cation corresponding to an amine, to form the bridged metallocene of formula (II), b) optionally separating off solid residues of the formula $M^1X$, c) optionally separating off the inert solvent or solvent mixture, d) recrystallizing the bridged metallocene of the formula (II) from an aprotic hydrocarbon, and e) separating the compound of the formula (II) from the mother liquor.

2. The process of claim 1 wherein in the bridged metallocenes of formula (IIa) and (II):

M is zirconium, $R^3$ are identical or different and are each hydrogen atom or a $C_{1-C10}$-alkyl, $C_2$–$C_{12}$-alkenyl, $C_6$–$C_{24}$-aryl, $C_5$–$C_{24}$-heteroaryl, $C_7$–$C_{30}$-arylalkyl, $C_7$–$C_{30}$-alkylaryl, fluorinated $C_6$–$C_{24}$-aryl, fluorinated $C_7$–$C_{30}$-arylalkyl, or fluorinated $C_7$–$C_{30}$-alkylaryl group, $R^4$, $R^6$ are identical or different and are each hydrogen atom or a $C_1$–$C_{18}$-alkyl, $C_2$–$C_{10}$-alkenyl, $C_3$–$C_{15}$-alkylalkenyl, $C_6$–$C_{18}$-aryl, $C_5$–$C_{18}$-heteroaryl, $C_7$–$C_{20}$-arylalkyl, $C_7$–$C_{20}$-alkylaryl, fluorinated $C_1$–$C_{12}$-alkyl, fluorinated $C_8$–$C_{18}$-aryl, fluorinated $C_7$–$C_{20}$-arylalkyl or fluorinated $C_7$–$C_{20}$-alkylaryl group, $R^8$, $R^9$ are identical or different and are each a hydrogen atom, a halogen atom, or a $C_1$–$C_{30}$-group, and two radicals $R^8$ and $R^9$ may form a monocyclic or polycyclic ring system which may in turn be substituted.

3. The process according to claim 1 where in the compounds of formula (IIa) and (II):

$R^5$, $R^7$ are hydrogen atoms,

X is chlorine,

Y is oxygen or sulfur, l, l' are 1, m' is 1, and

B is $(CH_3)_2Si$, $(CH_3)_2Ge$, $(C_6H_5)_2Si$, $(C_6H_5)(CH_3)Si$, $CH_2CH_2$, $CH(CH_3)CH_2$, $CH(CH_4H_g)C(CH_3)_2$, $CH_2$, $C(CH_3)_2$, or $(C_6H_5)_2C$.

4. A process according to claim 1 wherein a polar or nonpolar, aprotic hydrocarbon or hydrocarbon mixture is used in step d).

5. The process for converting a bridged metallocene of formula (IIa)

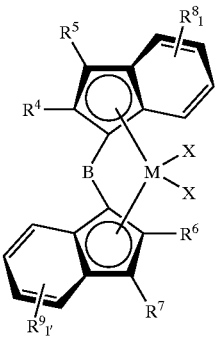

(IIa)

where

M is Ti, Zr or Hf, $R^4$, $R^6$ are identical or different and are each hydrogen or a $C_1$–$C_{30}$ group, $R^5$, $R^7$ are identical or different and are each a hydrogen atom or a $C_1$–$C_{20}$ group, $R^8$, $R^9$ are identical or different and are each a hydrogen atom, a halogen atom or a $C_{1-C30}$ group, and two radicals $R^8$ and $R^9$ may form a monocyclic or polycyclic ring system which may in turn be substituted, l, l' are identical or different and are each an integer from zero to 4, X is a halogen atom, and B is a bridging structural element between the two indenyl radicals, to a bridged metallocene of formula (II),

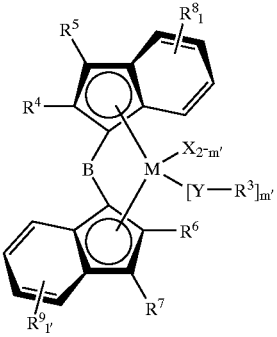

(II)

where

M, X, l, l', B, $R^4$, $R^5$, $R^6$, $R^7$, $R^8$ and $R^9$ have the same meaning as above, Y is an element of main group VI of the Periodic Table of the Elements, m' is 1 or 2, and $R^3$ are identical or different and are each halogen or a $C_1$–$C_{30}$ group;

comprising the steps a) reacting a bridged metallocene of the formula (IIa) with a ligand exchange component $M^1YR^3$ where Y and $R^3$ are as defined above, $M^1$ is a cation, a cationic fragment, or an ammonium cation corresponding to an amine, to form the bridged metallocene of formula (II), b) optionally separating off solid residues of the formula $M^1X$, c) optionally separating off the inert solvent or solvent mixture, d) recrystallizing the bridged metallocene of the formula (II) from a solvent selected from toluene, hexane, heptane, xylene, tetrahydrofuran (THF), diomethoxyethane (DME), toluene/THF, heptane/DME or toluene/DME, and e) separating the compound of the formula (II) from the mother liquor.

6. A process for converting a bridged metallocene of the formula (Ia)

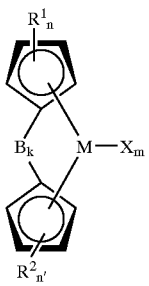

(Ia)

where

M is a metal of transition group III, IV, V or VI of the Periodic Table of the Elements, $R^1$ are identical or different and are each a radical $SiR^{12}_3$, where $R^{12}$ are identical or different and are each a hydrogen atom or a $C_1$–$C_{40}$ group, or $R^1$ is a $C_1$–$C_{30}$ group, or two or more radicals $R^1$ may be joined to one another in such a way that the radicals $R^1$ and the atoms of the cyclopentadienyl ring which connect them form a $C_4$–$C_{24}$-ring system which may in turn be substituted, $R^2$ are identical or different and are each a radical $SiR^{12}_3$, where $R^{12}$ are identical or different and are each a hydrogen atom or a $C_1$–$C_{40}$ group, or $R^2$ is a $C_1$–$C_{30}$ group, or two or more radicals $R^2$ may be joined to one another in such a way that the radicals $R^2$ and the atoms of the cyclopentadienyl ring which connect them form a $C_4$–$C_{24}$ ring system which may in turn be substituted, X is a halogen atom, n is from 0 to 4, n' is from 0 to 4, m is from 1 to 4, k is 1, and B is a bridging structural element between the two cyclopentadienyl rings,

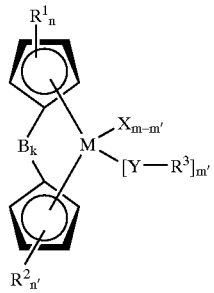

(I)

to a bridged metallocene of the formula (I)

where

M, $R^1$, $R^2$, X, n, n', m, k, B and $R^{12}$ are as defined above and m' is from 1 to 4, $R^3$ is hydrogen or a $C_1$–$C_{40}$ group, Y is an element of the main group 6 of the Periodic Table of the Elements, or a fragment $CR^3_2$, $NR^3$, $NR^3(CO)$—, $NR^3(SO_2)$—, $PR^3$ or $P(=O)R^3$, $O(CO)$—, $O(SO_2)$—, comprising the steps:

a) reacting the compound of the formula (Ia) with a ligand exchange component $M^1YR^3$ where Y and $R^3$ are as defined above, $M^1$ is a cation or a cationic fragment, with the compound of the formula $M^1X$, where $M^1$ and X are as defined above, being eliminated, in an inert solvent or solvent mixture, b) optionally, separating off solid residues of the formula $M^1X$ c) optionally, separating off the inert solvent or solvent mixture, d) recrystallizing the bridged metallocene of the formula (I) from an aprotic hydrocarbon, and e) separating the compound of the formula (I) from the mother liquor.

7. A process as claimed in claim 6, wherein a polar or nonpolar, aprotic hydrocarbon or hydrocarbon mixture is used in step d).

8. A process for converting a bridged metallocene of the formula (Ia)

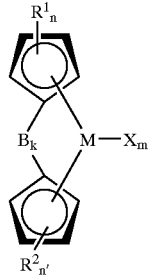

(Ia)

where

M is a metal of transition group III, IV, V or VI of the Periodic Table of the Elements, $R^1$ are identical or different and are each a radical $SiR^{12}{}_3$, where $R^{12}$ are identical or different and are each a hydrogen atom or a $C_1$–$C_{40}$ group, or $R^1$ is a $C_1$–$C_{30}$ group, or two or more radicals $R^1$ may be joined to one another in such a way that the radicals $R^1$ and the atoms of the cyclopentadienyl ring which connect them form a $C_4$–$C_{24}$-ring system which may in turn be substituted, $R^2$ are identical or different and are each a radical $SiR^{12}{}_3$, where $R^{12}$ are identical or different and are each a hydrogen atom or a $C_1$–$C_{40}$ group, or $R^2$ is a $C_1$–$C_{30}$ group, or two or more radicals $R^2$ may be joined to one another in such a way that the radicals $R^2$ and the atoms of the cyclopentadienyl ring which connect them form a $C_4$–$C_{24}$ ring system which may in turn be substituted, X is a halogen atom, n is from 0 to 4, n' is from 0 to 4, m is from 1 to 4, k is 1, and B is a bridging structural element between the two cyclopentadienyl rings, to a bridged metallocene of the formula (I)

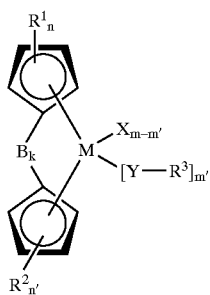

(I)

where

M, $R^1$, $R^2$, X, n, n', m, k, B and $R^{12}$ are as defined above and m' is from 1 to 4, $R^3$ is hydrogen or a $C_1$–$C_{40}$ group, Y is an element of the main group 6 of the Periodic Table of the Elements, or a fragment $CR^3{}_2$, $NR^3$, $NR^3(CO)$—, $NR^3(SO_2)$—, $PR^3$ or $P(=O)R^3$, $O(CO)$—, $O(SO_2)$—, comprising the steps:

a) reacting the compound of the formula (Ia) with a ligand exchange component

 $M^1YR^3$ where

Y and $R^3$ are as defined above, $M^1$ is a cation or a cationic fragment, or is an ammonium cation corresponding to an amine, with the compound of the formula $M^1X$, where $M^1$ and X are as defined above, being eliminated, in an inert solvent or solvent mixture, b) optionally, separating off solid residues of the formula $M^1X$ c) optionally, separating off the inert solvent or solvent mixture, d) recrystallizing the bridged metallocene of the formula (I) from a solvent selected from toluene, hexane, heptane, xylene, tetrahydrofuran (THF), dimethoxyethane (DME), toluene/THF, heptane/DME or toluene/DME, and e) separating the compound of the formula (I) from the mother liquor.

9. The process according to claim 6, where in the bridged metallocenes of formula (I) and (Ia):

M is Ti, Zr or Hf,

R' are identical or different and are each a radical $SiR^{12}{}_3$, where $R^{12}$ are identical or different and are each a hydrogen atom or $C_1$–$C_{20}$-alkyl, $C_1$–$C_{10}$-fluoroalkyl, $C_1$–$C_{10}$-alkoxy, $C_6$–$C_{20}$-aryl, $C_6$–$C_{10}$-fluoroaryl, $C_6$–$C_{10}$-aryloxy, $C_2$–$C_{10}$-alkenyl, $C_7$–$C_{40}$-arylalkyl, $C_7$–$C_{40}$-alkylaryl or $C_8$–$C_{40}$-arylalkenyl, or $R^1$ is $C_1$–$C_{25}$-alkyl such as methyl, ethyl, tert-butyl, cyclohexyl or octyl, $C_2$–$C_{25}$-alkenyl, $C_3$–$C_{15}$-alkylalkenyl, $C_8$–$C_{24}$-aryl, $C_5$–$C_{24}$-heteroaryl, $C_7$–$C_{30}$-arylalkyl, $C_7$–$C_{30}$-alkylaryl, fluorinated $C_1$–$C_{25}$-alkyl, fluorinated $C_6$–$C_{24}$-aryl, fluorinated $C_7$–$C_{30}$-arylalkyl, fluorinated $C_7$–$C_{30}$-alkylaryl or $C_1$–$C_{12}$-alkoxy, or two or more radicals $R^1$ may be joined to one another in such a way that the radicals $R^1$ and the atoms of the cyclopentadienyl ring which connect them form a $C_4$–$C_{24}$-ring system which may in turn be substituted, $R^2$ are identical or different and are each a radical $SiR^{12}{}_3$, where $R^{12}$ are identical or different and are each a hydrogen atom or $C_1$–$C_{20}$-alkyl, $C_1$–$C_{10}$-fluoroalkyl, $C_1$–$C_{10}$-alkoxy, $C_6$–$C_{14}$-aryl, $C_6$–$C_{10}$-fluoroaryl, $C_6$–$C_{10}$-aryloxy, $C_2$–$C_{10}$-alkenyl, $C_7$–$C_{40}$-arylalkyl, $C_7$–$C_{40}$-alkylaryl or $C_8$–$C_{40}$-arylalkenyl, or $R^2$ is $C_1$–$C_{25}$-alkyl such as methyl, ethyl, tert-butyl, cyclohexyl or octyl, $C_2$–$C_{25}$-alkenyl, $C_3$–$C_{15}$-alkylalkenyl, $C_6$–$C_{24}$-aryl, $C_5$–$C_{24}$-heteroaryl, $C_7$–$C_{30}$-arylalkyl, $C_7$–$C_{30}$-alkylaryl, fluorinated $C_1$–$C_{25}$-alkyl, fluorinated $C_6$–$C_{24}$-aryl, fluorinated $C_7$–$C_{30}$-arylalkyl, fluorinated $C_7$–$C_{30}$-alkylaryl or $C_1$–$C_{12}$-alkoxy, or two or more radicals $R^2$ may be joined to one another in such a way that the radicals $R^2$ and the atoms of the cyclopentadienyl ring which connect them form a $C_4$–$C_{24}$ ring system which may in turn be substituted, or two or more radicals $R^2$ may be joined to one another in such a way that the radicals $R^2$ and the atoms of the cyclopentadienyl ring which connect them form a $C_4$–$C_{24}$ ring system which may in turn be substituted, $R^3$ is hydrogen or $C_1$–$C_{25}$-alkyl, $C_2$–$C_{25}$-alkenyl, $C_3$–$C_{15}$-alkylalkenyl, $C_6$–$C_{24}$-aryl, $C_5$–$C_{24}$-heteroaryl, $C_7$–$C_{30}$-arylalkyl, $C_7$–$C_{30}$-alkylaryl, fluorinated $C_1$–$C_{25}$-alkyl, fluorinated $C_6$–$C_{24}$-aryl, fluorinated $C_7$–$C_{30}$-arylalkyl or fluorinated $C_7$–$C_{30}$-alkylaryl, Y is an element of main group 6 of the Periodic Table of Elements.

10. A process for converting a bridged metallocene of the formula (Ia)

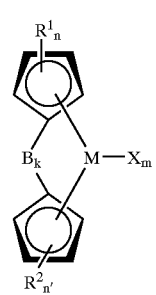

(Ia)

where

M is a metal of transition group III, IV, V or VI of the Periodic Table of the Elements, $R^1$ are identical or different and are each a radical $SiR^{12}_3$, where $R^{12}$ are identical or different and are each a hydrogen atom or a $C_1$–$C_{40}$ group, or $R^1$ is a $C_1$–$C_{30}$ group, or two or more radicals $R^1$ may be joined to one another in such a way that the radicals $R^1$ and the atoms of the cyclopentadienyl ring which connect them form a $C_4$–$C_{24}$-ring system which may in turn be substituted, $R^2$ are identical or different and are each a radical $SiR^{12}_3$, where $R^{12}$ are identical or different and are each a hydrogen atom or a $C_1$–$C_{40}$ group, or $R^2$ is a $C_1$–$C_{30}$ group, or two or more radicals $R^2$ may be joined to one another in such a way that the radicals $R^2$ and the atoms of the cyclopentadienyl ring which connect them form a $C_4$–$C_{24}$ ring system which may in turn be substituted, X is a halogen atom, n is from 0 to 4, n' is from 0 to 4, m is from 1 to 4, k is 1, and B is a bridging structural element between the two cyclopentadienyl rings,

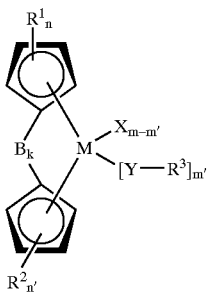

(I)

to a bridged metallocene of the formula (I) where M, $R^1$, $R^2$, X, n, n', m, k, B and $R^{12}$ are as defined above and m' is from 1 to 4, $R^3$ is hydrogen or a $C_1$–$C_{40}$ group, Y is an element of the main group 6 of the Periodic Table of the Elements, or a fragment $CR^3_2$, $NR^3$, $NR^3(CO)$—, $NR^3(SO_2)$—, $PR^3$ or $P(=O)R^3$, $O(CO)$—, $O(SO_2)$—, and in which one or both cyclopentadienyl rings of the bridged metallocene of formula (I) and (Ia) are substituted in such a way that they form an indenyl ring, comprising the steps:

a) reacting the compound of the formula (Ia) with a ligand exchange component $M^1YR^3$ where Y and $R^3$ are as defined above, $M^1$ is a cation or a cationic fragment, in particular Li, Na, K, MgCl, MgBr, MgI, or is an ammonium cation corresponding to an amine, with the compound of the formula $M^1X$, where $M^1$ and X are as defined above, being eliminated, in an inert solvent or solvent mixture, b) optionally, separating off solid residues of the formula $M^1X$ c) optionally, separating off the inert solvent or solvent mixture, d) recrystallizing the bridged metallocene of the formula (I) from an aprotic hydrocarbon, and e) separating the compound of the formula (I) from the mother liquor.

11. A process as claimed in claim 10, wherein a polar or nonpolar, aprotic hydrocarbon or hydrocarbon mixture is used in step d).

12. A process for converting a bridged metallocene of the formula (Ia)

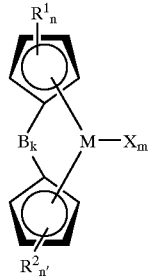

(Ia)

where

M is a metal of transition group III, IV, V or VI of the Periodic Table of the Elements, $R^1$ are identical or different and are each a radical $SiR^{12}_3$, where $R^{12}$ are identical or different and are each a hydrogen atom or a $C_1$–$C_{40}$ group, or $R^1$ is a $C_1$–$C_{30}$ group, or two or more radicals $R^1$ may be joined to one another in such a way that the radicals $R^1$ and the atoms of the cyclopentadienyl ring which connect them form a $C_4$–$C_{24}$-ring system which may in turn be substituted, $R^2$ are identical or different and are each a radical $SiR^{12}_3$, where $R^{12}$ are identical or different and are each a hydrogen atom or a $C_1$–$C_{40}$ group, or $R^2$ is a $C_1$–$C_{30}$ group, or two or more radicals $R^2$ may be joined to one another in such a way that the radicals $R^2$ and the atoms of the cyclopentadienyl ring which connect them form a $C_4$–$C_{24}$ ring system which may in turn be substituted, X is a halogen atom, n is from 0 to 4, n' is from to 4, m is from 1 to 4, k is 1, and B is a bridging structural element between the two cyclopentadienyl rings, to a bridged metallocene of the formula (I)

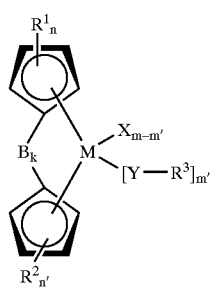

(I)

where

M, $R^1$, $R^2$, X, n, n', m, k, B and $R^{12}$ are as defined above and m' is from 1 to 4, $R^3$ is hydrogen or a $C_1$–$C_{40}$ group, Y is an element of the main group 6 of the Periodic Table of the Elements, or a fragment $CR^3{}_2$, $NR^3$, $NR^3(CO)$—, $NR^3(SO_2)$—, $PR^3$ or $P(=O)R^3$, $O(CO)$—, $O(SO)$—, and in which one or both cyclopentadienyl rings of the bridged metallocene of formula (I) and (Ia) are substituted in such a way that they form an indenyl ring, comprising the steps:

a) reacting the compound of the formula (Ia) with a ligand exchange component $M^1YR^3$ where Y and $R^3$ are as defined above, $M^1$ is a cation or a cationic fragment, or is an ammonium cation corresponding to an amine, with the compound of the formula $M^1X$, where $M^1$ and X are as defined above, being eliminated, in an inert solvent or solvent mixture, b) optionally, separating off solid residues of the formula $M^1X$ c) optionally, separating off the inert solvent or solvent mixture, d) recrystallizing the bridged metallocene of the formula (I) from a solvent selected from toluene, hexane, heptane, xylene, tetrahydrofuran (THF), dimethoxyethane (DME), toluene/THF, heptane/DME or toluene/DME, and e) separating the compound of the formula (I) from the mother liquor.

13. The process according to claim 10, where in the bridged metallocenes of formula (I) and (Ia):

M is Ti, Zr or Hf, $R^1$ are identical or different and are each a radical $SiR^{12}{}_3$, where $R^{12}$ are identical or different and are each a hydrogen atom or $C_1$–$C_{20}$-alkyl, $C_1$–$C_{10}$-fluoroalkyl, $C_1$–$C_{10}$-alkoxy, $C_6$–$C_{20}$-aryl, $C_6$–$C_{10}$-fluoroaryl, $C_6$–$C_{10}$-aryloxy, $C_2$–$C_{10}$-alkenyl, $C_7$–$C_{40}$-arylalkyl, $C_7$–$C_{40}$-alkylaryl or $C_8$–$C_{40}$-arylalkenyl, or $R^1$ is $C_1$–$C_{25}$alkyl such as methyl, ethyl, tert-butyl, cyclohexyl or octyl, $C_2$–$C_{25}$-alkenyl, $C_3$–$C_{15}$-alkylalkenyl, $C_6$–$C_{24}$-aryl, $C_5$–$C_{24}$-heteroaryl, $C_7$–$C_{30}$-arylalkyl $C_7$–$C_{30}$-alkylaryl, fluorinated $C_1$–$C_{25}$-alkyl, fluorinated $C_6$–$C_{24}$-aryl, fluorinated $C_7$–$C_{30}$-arylalkyl, fluorinated $C_7$–$C_{30}$-alkylaryl or $C_1$–$C_{12}$-alkoxy, or two or more radicals $R^1$ may be joined to one another in such a way that the radicals $R^1$ and the atoms of the cyclopentadienyl ring which connect them form a $C_4$–$C_{24}$-ring system which may in turn be substituted, $R^2$ are identical or different and are each a radical $SiR^{12}{}_3$, where $R^{12}$ are identical or different and are each a hydrogen atom or $C_1$–$C_{20}$-alkyl, $C_1$–$C_{10}$-fluoroalkyl, $C_1$–$C_{10}$-alkoxy, $C_6$–$C_{14}$-aryl, $C_6$–$C_{10}$-fluoroaryl, $C_8$–$C_{10}$-aryloxy, $C_2$–$C_{10}$-alkenyl, $C_7$–$C_{40}$-arylalkyl, $C_7$–$C_{40}$-alkylaryl or $C_8$–$C_{40}$-arylalkenyl, or $R^2$ is $C_1$–$C_{25}$-alkyl such as methyl, ethyl, tert-butyl, cyclohexyl or octyl, $C_2$–$C_{25}$-alkenyl, $C_3$–$C_{15}$-alkylalkenyl, $C_6$–$C_{24}$-aryl, $C_5$–$C_{24}$-heteroaryl, $C_7$–$C_{30}$-arylalkyl, $C_7$–$C_{30}$-alkylaryl, fluorinated $C_1$–$C_{25}$-alkyl, fluorinated $C_6$–$C_{24}$-aryl, fluorinated $C_7$–$C_{30}$-arylalkyl, fluorinated $C_7$–$C_{30}$-alkylaryl or $C_1$–$C_{12}$-alkoxy, or two or more radicals $R^2$ may be joined to one another in such a way that the radicals $R^2$ and the atoms of the cyclopentadienyl ring which connected them form a $C_4$–$C_{24}$ ring system which may in turn be substituted, or two or more radicals $R^2$ may be joined to one another in such a way that the radicals $R^2$ and the atoms of the cyclopentadienyl ring which connect them form a $C_4$–$C_{24}$ ring system which may in turn be substituted, $R^3$ is hydrogen or $C_1$–$C_{25}$-alkyl, $C_2$–$C_{25}$-alkenyl $C_3$–$C_{15}$-alkylalkenyl, $C_6$–$C_{24}$-aryl, $C_5$–$C_{24}$-heteroaryl, $C_7$–$C_{30}$alkylaryl, $C_7$–$C_{30}$-alkylaryl, fluorinated $C_1$–$C_{25}$-alkyl, fluorinated $C_6$–$C_{24}$-aryl, fluorinated $C_7$–$C_{30}$-arylalkyl or fluorinated $C_7$–$C_{30}$-alkylaryl, Y is an element of main group 6 of the Periodic Table of Elements.

14. A process as claimed in claim 6, wherein $M^1$ is Li, Na, K, MgCl, MgBr, MgI, or is an ammonium cation corresponding to an amine.

* * * * *